United States Patent
Dekleva et al.

(10) Patent No.: US 9,651,520 B2
(45) Date of Patent: May 16, 2017

(54) MICROFLUIDIC INTERFACE FOR A MICROCHIP

(75) Inventors: Philippe M. Dekleva, Fort Collins, CO (US); Jonathan A. Vickers, Fort Collins, CO (US); James T. Palmer, Loveland, CO (US)

(73) Assignee: Mettler-Toledo Thornton, Inc., Bedford, MA (US)

( * ) Notice: Subject to any disclaimer, the term of this patent is extended or adjusted under 35 U.S.C. 154(b) by 1298 days.

(21) Appl. No.: 13/988,055

(22) PCT Filed: Feb. 25, 2011

(86) PCT No.: PCT/US2011/000348
§ 371 (c)(1),
(2), (4) Date: May 17, 2013

(87) PCT Pub. No.: WO2011/106098
PCT Pub. Date: Sep. 1, 2011

(65) Prior Publication Data
US 2013/0248369 A1    Sep. 26, 2013

Related U.S. Application Data

(60) Provisional application No. 61/338,971, filed on Feb. 25, 2010.

(51) Int. Cl.
  *G01N 27/447*  (2006.01)
  *B01L 3/00*  (2006.01)
  *B81B 1/00*  (2006.01)
  *B01L 9/00*  (2006.01)

(52) U.S. Cl.
CPC .. *G01N 27/44791* (2013.01); *B01L 3/502715* (2013.01); *B01L 3/502776* (2013.01); *B81B 1/00* (2013.01); *B01L 3/502753* (2013.01); *B01L 9/527* (2013.01); *B01L 2300/0816* (2013.01); *B01L 2300/0867* (2013.01); *B01L 2400/0421* (2013.01)

(58) Field of Classification Search
CPC ......... B01L 3/502715; B01L 3/502776; B01L 3/502753; B01L 3/5027; B01L 9/527; B01L 2300/0867; B01L 2300/0816; B01L 2300/0654; B01L 2400/0421; B01L 2200/025; B01L 2200/026; B01L 2200/027; B01L 2200/04; G01N 27/44791; G01N 27/44704
See application file for complete search history.

(56) References Cited

U.S. PATENT DOCUMENTS

| 5,126,023 A | 6/1992 | Huang et al. |
| 5,298,139 A | 3/1994 | Huang et al. |
| 5,429,734 A | 7/1995 | Gajar et al. |
| 5,545,303 A | 8/1996 | Schasfoort et al. |

(Continued)

OTHER PUBLICATIONS

Oh et al., Lab Chip, 2005, 845-850.*

(Continued)

*Primary Examiner* — Gurpreet Kaur
(74) *Attorney, Agent, or Firm* — Standley Law Group LLP

(57) ABSTRACT

A capillary electrophoresis system which provides a microfluidic chip for capillary electrophoresis and a microfluidic interface module which fluidicly couples the microfluidic chip to external fluid sources and or external repositories.

17 Claims, 23 Drawing Sheets

(56) References Cited

U.S. PATENT DOCUMENTS

| | | |
|---|---|---|
| 6,143,152 A | 11/2000 | Simpson et al. |
| 6,162,341 A | 12/2000 | Nordman et al. |
| 6,491,804 B2 | 12/2002 | Manz et al. |
| 6,491,844 B1 | 12/2002 | Shepodd |
| 6,699,377 B2 | 3/2004 | Manz et al. |
| 6,699,378 B2 | 3/2004 | Manz et al. |
| 6,706,164 B2 | 3/2004 | Manz et al. |
| 6,730,202 B2 | 5/2004 | Manz et al. |
| 6,878,255 B1 | 4/2005 | Wang et al. |
| 6,960,286 B2 | 11/2005 | Manz et al. |
| 6,974,678 B2 | 12/2005 | Wilson et al. |
| 7,090,758 B2 | 8/2006 | Mathies et al. |
| 7,344,628 B2 | 3/2008 | Jackson et al. |
| 7,465,317 B2 | 12/2008 | Malberg et al. |
| 7,582,263 B2 * | 9/2009 | Prak .............. B01L 9/527 204/403.01 |
| 7,740,747 B2 | 6/2010 | Tian et al. |
| 7,885,490 B2 | 2/2011 | Heideman et al. |
| 8,012,328 B2 | 9/2011 | Henry et al. |
| 8,080,421 B2 | 12/2011 | DeLucas et al. |
| 8,262,884 B2 | 9/2012 | Sideris |
| 8,354,077 B2 | 1/2013 | Prak et al. |
| 2004/0009517 A1 | 1/2004 | Ramsey |
| 2004/0067577 A1 | 4/2004 | Wilson et al. |
| 2005/0109621 A1 | 5/2005 | Hauser et al. |
| 2006/0144710 A1 | 7/2006 | Bastemeijer et al. |
| 2008/0014576 A1 * | 1/2008 | Jovanovich .......... B01F 11/0071 435/5 |
| 2008/0135410 A1 | 6/2008 | Henry et al. |
| 2008/0230389 A1 | 9/2008 | Ha et al. |
| 2011/0008223 A1 * | 1/2011 | Tsao .................. B01L 3/502715 422/502 |

OTHER PUBLICATIONS

U.S. Appl. No. 61/338,971, filed Feb. 25, 2010.
PCT Interantional Patent Application No. PCT/US2011/000348, filed Feb. 25, 2011.
Giblin, et al. Rapid Detection of Perchlorate in Groundwater Using Capilary Electrophoresis. Chromatographia, 2000, 52, pp. 502-508, Vieweg Verlag, Germany.
Li et al. Determination of chloride, chlorate and perchlorate by PDMS microchip electrophoresis with indirect amperometric detection. Talanta, Mar. 2008, vol. 75, pp. 157-162.
Liu, et al. Simple and Sensitive Electrode Design for Microchip Electrophoresis/Electrochemistry. Analytical Chemistry, Mar. 2004, vol. 76, issue 5, pp. 1513-1517.

* cited by examiner

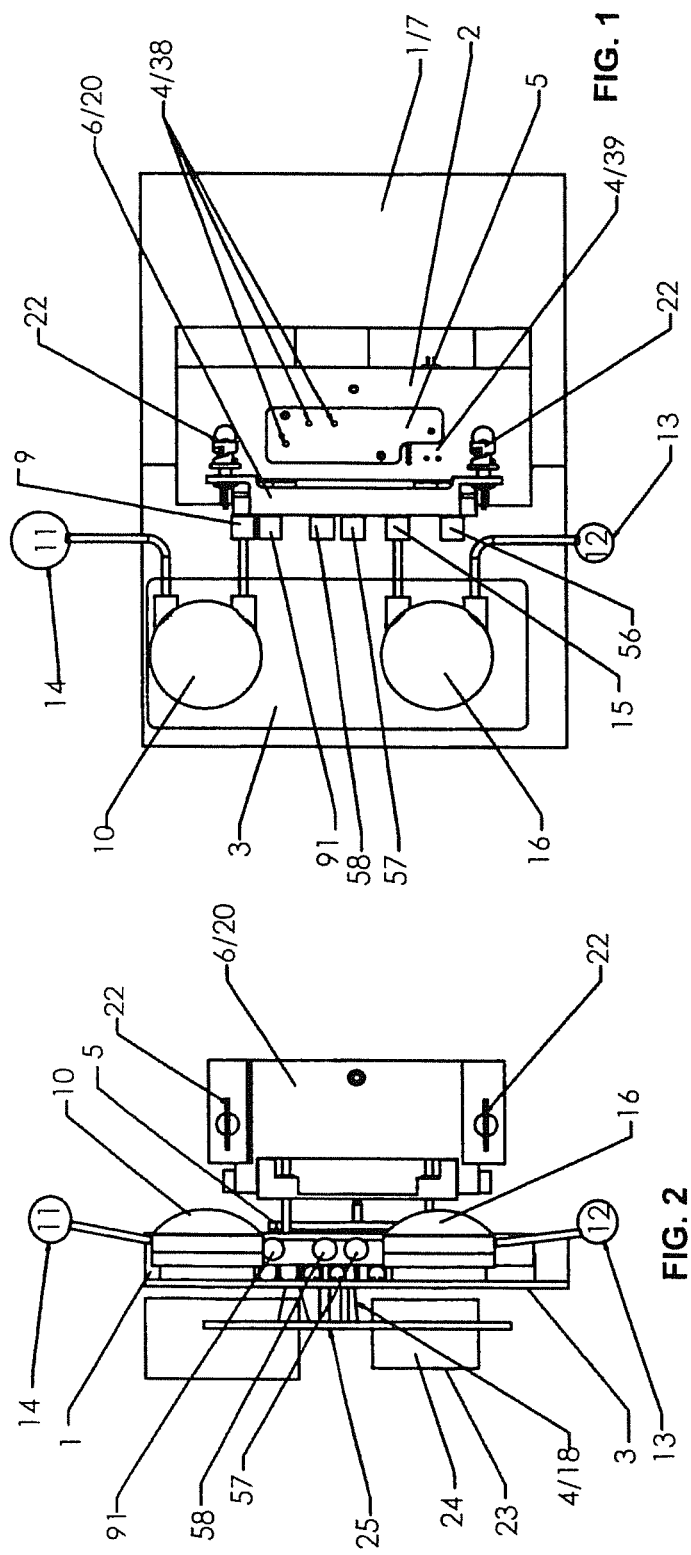
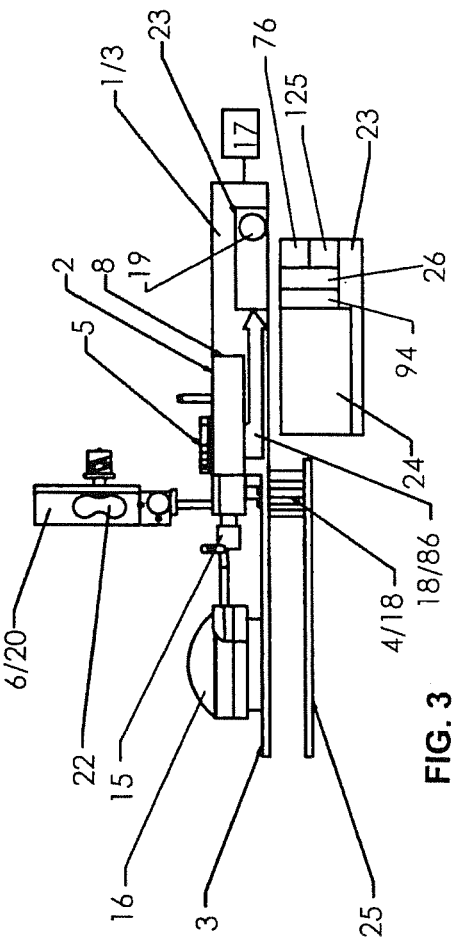

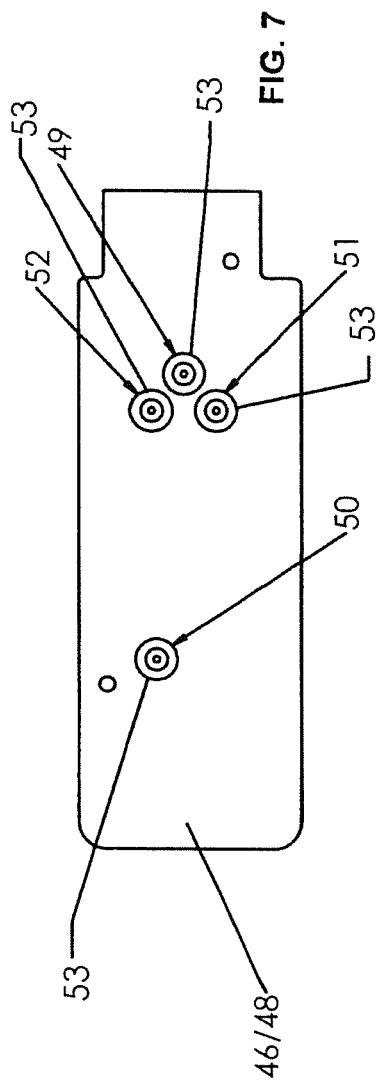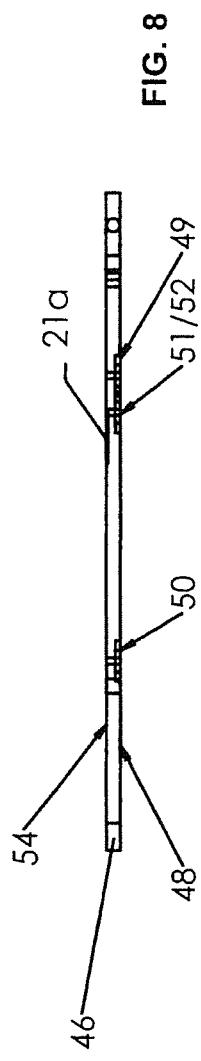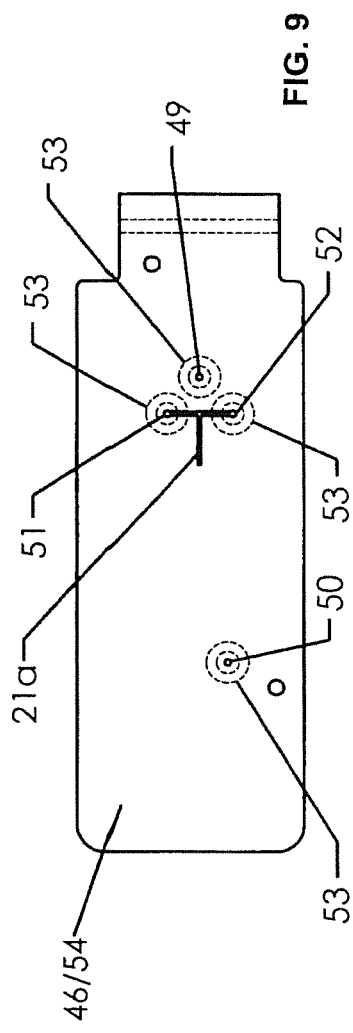

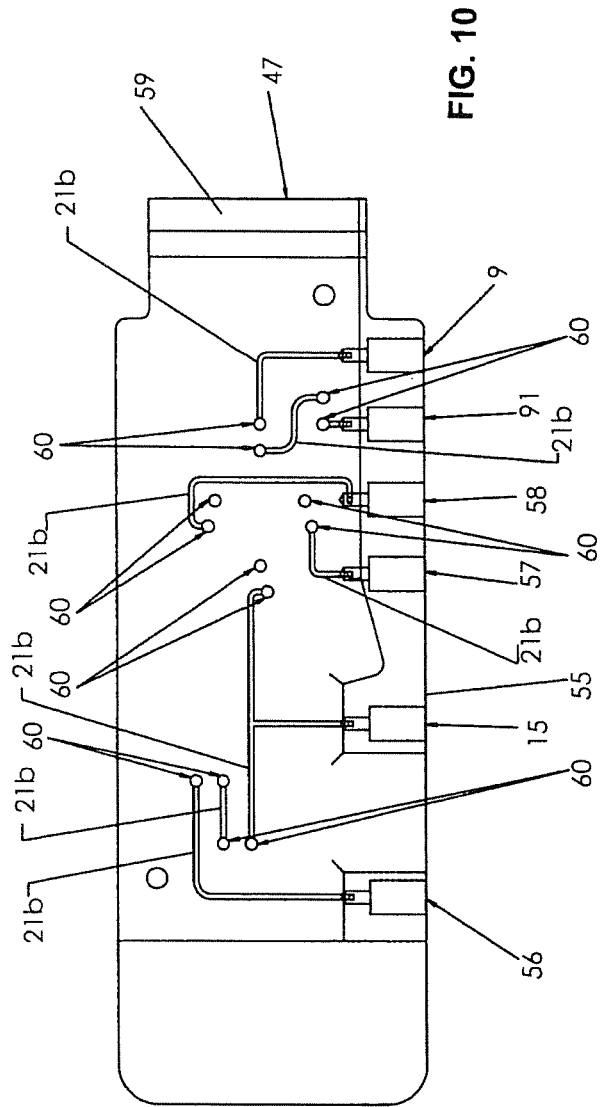
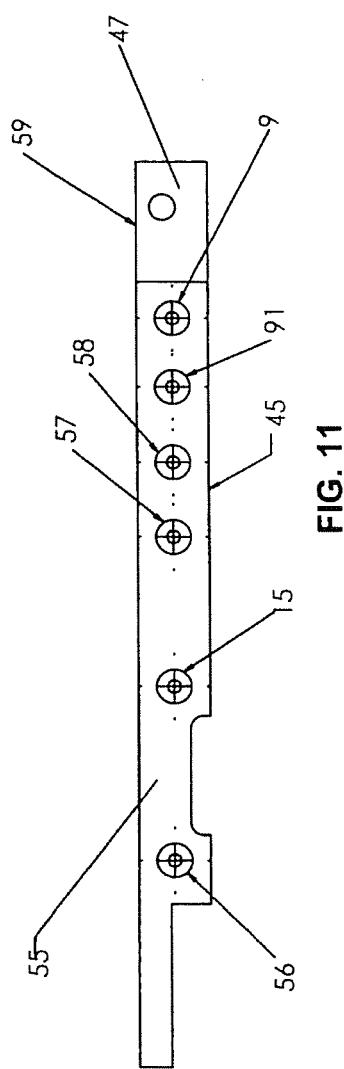

| | VALVE 1 | VALVE 2 | VALVE 3 | VALVE 4 | VALVE 5 | VALVE 6 | VALVE 7 |
|---|---|---|---|---|---|---|---|
| PRIME | OPEN | SHORT OPEN THEN CLOSED | DELAYED OPEN | OPEN | OPEN | CLOSED | OPEN |
| SAMPLE LOAD | CLOSED | CLOSED | CLOSED | OPEN | OPEN | OPEN | CLOSED |
| SAMPLE ANALYSIS | CLOSED | CLOSED | CLOSED | CLOSED | CLOSED | CLOSED | CLOSED |
| FLUSH | OPEN | CLOSED | CLOSED | OPEN | OPEN | CLOSED | OPEN |

| PROCEDURE | VALVE 1 | VALVE 2 | VALVE 3 | VALVE 4 | VALVE 5 | VALVE 6 | VALVE 7 |
|---|---|---|---|---|---|---|---|
| PRIME | SHORT OPEN THEN CLOSED | OPEN | DELAYED OPEN | OPEN | OPEN | CLOSED | OPEN |
| SAMPLE LOAD | CLOSED | CLOSED | CLOSED | OPEN | OPEN | OPEN | CLOSED |
| SAMPLE ANALYSIS | CLOSED | CLOSED | CLOSED | CLOSED | CLOSED | CLOSED | CLOSED |
| FLUSH | CLOSED | OPEN | CLOSED | OPEN | OPEN | CLOSED | OPEN |

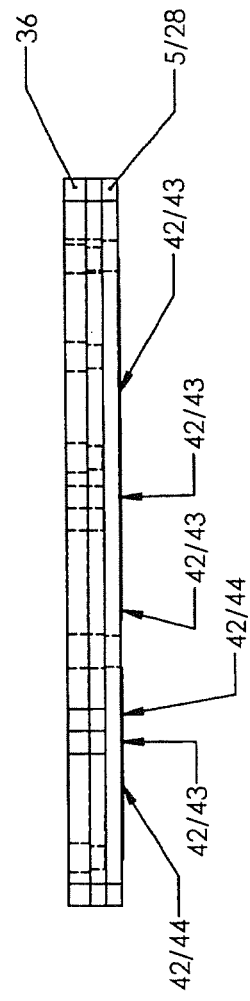
FIG. 29
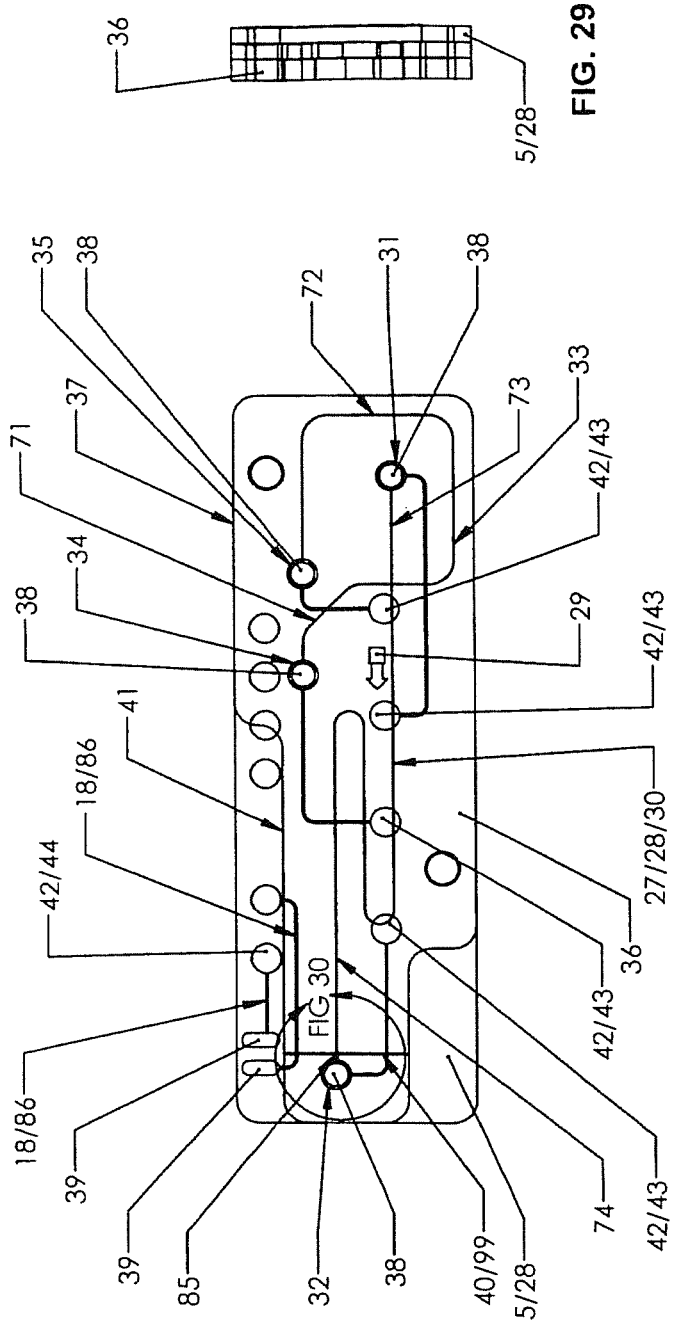
FIG. 27
FIG. 28

MICROFLUIDIC INTERFACE FOR A MICROCHIP

This application is the United States National Stage of International Patent Cooperation Treaty Patent Application No. PCT/US2011/000348, filed Feb. 25, 2011, which claims the benefit of U.S. Patent Application 61/338,971, filed Feb. 25, 2010, hereby incorporated by reference herein.

I. TECHNICAL FIELD

A capillary electrophoresis system which provides a microfluidic chip for capillary electrophoresis and a microfluidic interface module which fluidicly couples the microfluidic chip to external fluid sources and or external repositories.

II. BACKGROUND

Conventional microfluidic chips for capillary electrophoresis typically provide a carrier channel in which substances within a sample are electrophoretically separated and detected and a sample channel which intersects with the carrier sample for introduction of samples into the carrier channel. Typically, the carrier channel is fluidically disposed between a pair of carrier fluid reservoirs and the sample channel is disposed between a pair of sample reservoirs. A sample fluid containing substances for separation can be introduced into a sample reservoir and the carrier fluid which provides an electrically conductive medium is introduced into a carrier reservoir manually by dropper, syringe, or the like. The sample fluid and the carrier fluid typically flow through the network of channels by capillary action, external pressure or electro-osmotic flow.

A voltage in the range of few hundred volts and sometimes above a thousand volts can be applied between the reservoirs through electrical probes. This induces an electro-osmotic flow which can be used to entrain a small amount of the sample fluid into the carrier channel at the intersection of the two channels. The various charged substances in the small amount of sample will separate in the carrier channel as a consequence of differences in electrophoretic mobility. At a certain location, the fluid in the carrier channel may be interrogated either optically or electrically. Due to separation of the various substances within the carrier channel each can pass the detection location at different times. This provides a means for resolving the various substances within the sample.

While conventional microfluidic chips for capillary electrophoresis may efficiently separate certain substances within a sample fluid, the conventional handling, timing and delivery of sample fluids, carrier fluids or other fluids to flow paths of the microfluidic chip, and particularly the manual transfer of fluids to the corresponding reservoirs of the microfluidic chip, precludes an automated capillary electrophoresis system for sample analysis.

III. DISCLOSURE OF INVENTION

Accordingly, a broad object of the invention can be to provide a microfluidic interface which engages a microfluidic chip to provide sealed fluidic couplings between one or more external sample fluid sources, a carrier fluid source, and external repositories and the flow paths within a microfluidic chip.

Another broad object of the invention can be to provide a microfluidic interface which engages a microfluidic chip to provide sealed fluidic couplings between external fluid sources and external repositories and the flow paths within a microfluidic which allows carrier fluid and sample fluid to be loaded into a sealed capillary electrophoresis system.

Another broad object of the invention can be to provide a plurality of microfluidic valves operable between an open condition and a closed condition in response to signals generated by a computer implemented (or electromechanically or manually implemented) event schedule which allows ingress and egress of sample fluid(s) and carrier fluid(s) or other fluids in relation to the flow paths of a microfluidic chip for serial manual or automated sample loading, capillary electrophoresis, and analysis of a plurality of sample fluids within a microfluidic electrophoresis system whether in a sealed condition or in an open condition.

Another broad object of the invention can be to provide a general constructional form of a microfluidic interface which can be adopted to a wide variety of configurations of flow paths within a microfluidic chip which correspondingly allows for utilization of a numerous and wide variety of methods of sample handling or analysis within a microfluidic chip.

Another broad object of the invention can be to provide a microfluidic interface which engages a microfluidic chip to provide sealed fluidic couplings between external fluid sources and external repositories and the flow paths within a microfluidic chip which allows carrier fluid and a sample fluid to be loaded in a sealed capillary electrophoresis system and allows analysis of the sample fluid in either a sealed or open microfluidic chip.

Another broad object of the invention can be to provide a microfluidic interface which engages a microfluidic chip to provide sealed fluidic couplings between external fluid sources and external repositories and the flow paths within a microfluidic chip which allows carrier fluid and a sample fluid to be loaded by a method which flushes entrapped gas from the flow paths of the microfluidic chip.

Another broad object of the invention can be to provide a microfluidic interface which engages a microfluidic chip to provide sealed fluidic coupling with sample reservoirs and carrier fluid reservoirs configured to purge liquid and displace entrapped gas within the reservoirs in isolation to the remaining portion of the flow paths within the microfluidic chip.

Naturally, further objects of the invention are disclosed throughout other areas of the specification, drawings, photographs, and claims.

IV. BRIEF DESCRIPTION OF THE DRAWINGS

FIG. 1 is a top view of a particular embodiment of the invention.

FIG. 2 is a back view of a particular embodiment of the invention.

FIG. 3 is a side view of a particular embodiment of the invention.

FIG. 7 is a top view of a first side of a particular embodiment of the first microfluidic interface layer of the microfluidic interface module.

FIG. 8 is a side view of a first side of a particular embodiment of the first microfluidic interface layer of the microfluidic interface module.

FIG. 9 is a side view of a second side of a particular embodiment of the first microfluidic interface layer of the microfluidic interface module.

FIG. 10 is a top view of a second side of a particular embodiment of the second microfluidic interface layer of the microfluidic interface module.

FIG. 11 is a side view of a particular embodiment of the second microfluidic interface layer of the microfluidic interface module.

Figure 14:
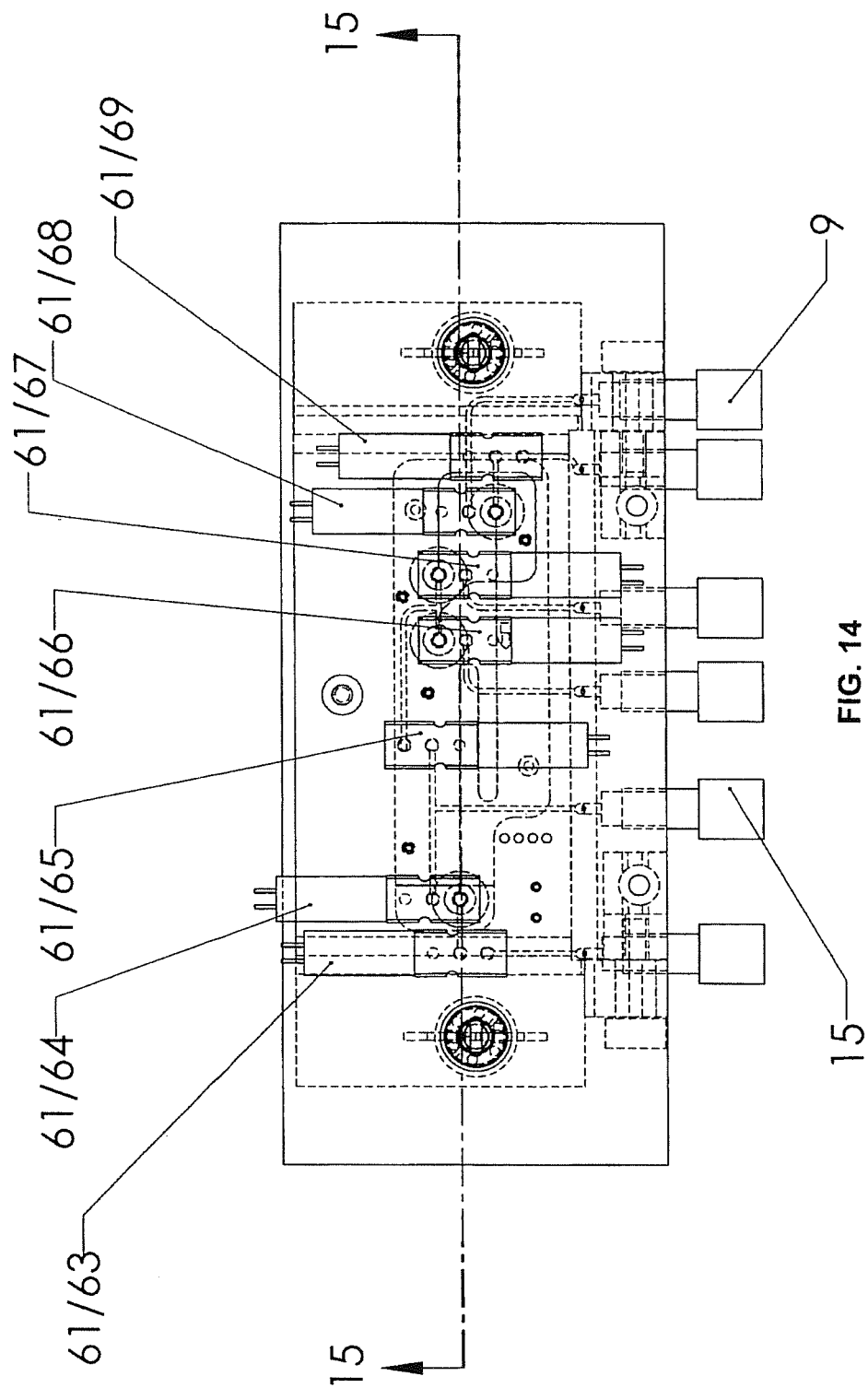

FIG. 14 a top view of a particular embodiment of the microfluidic interface module.

Figure 15:
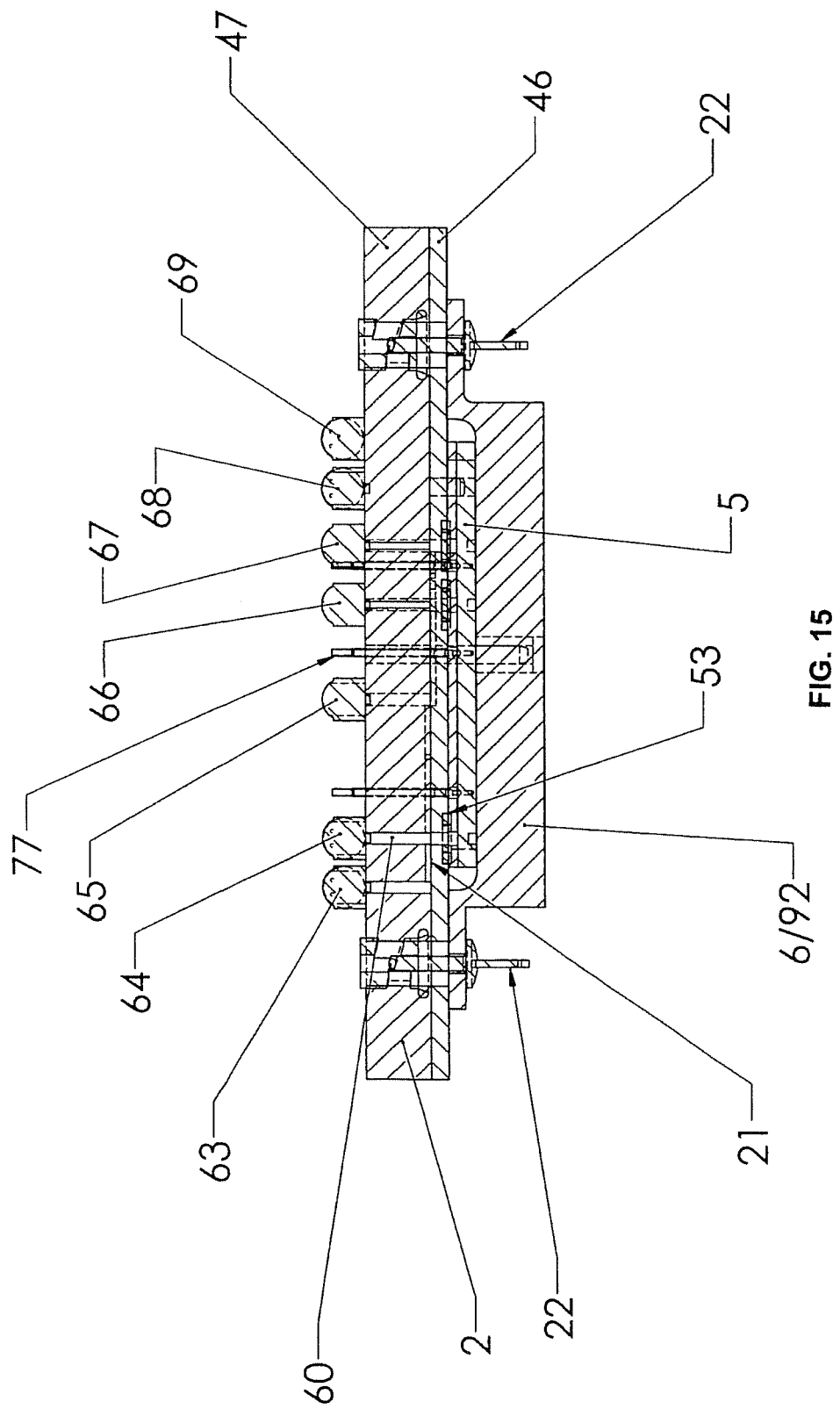

FIG. 15 is a cross section 15-15 view of the particular embodiment of the microfluidic interface module shown in FIG. 14.

Figure 16:
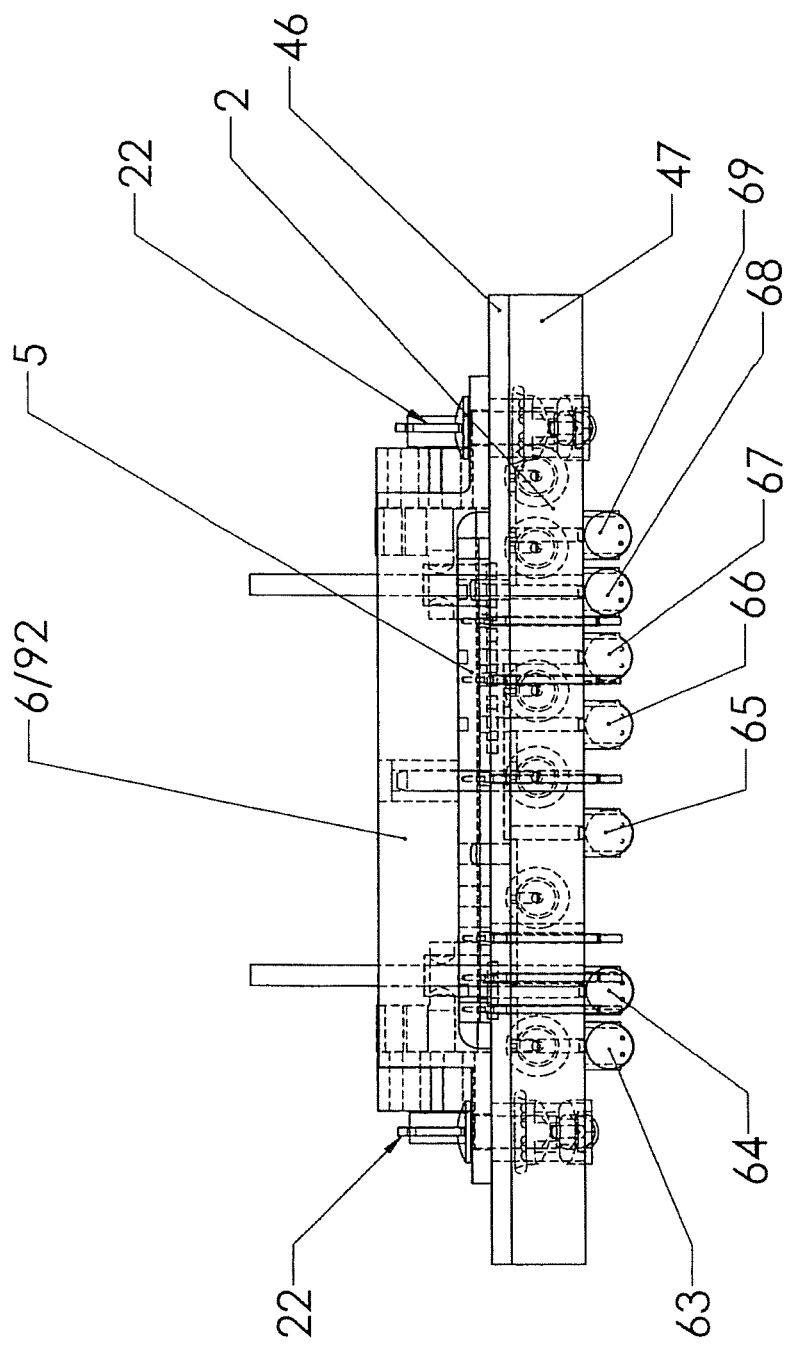

FIG. 16 is a side view of the particular embodiment of the microfluidic interface module shown in FIG. 14.

Figure 17:
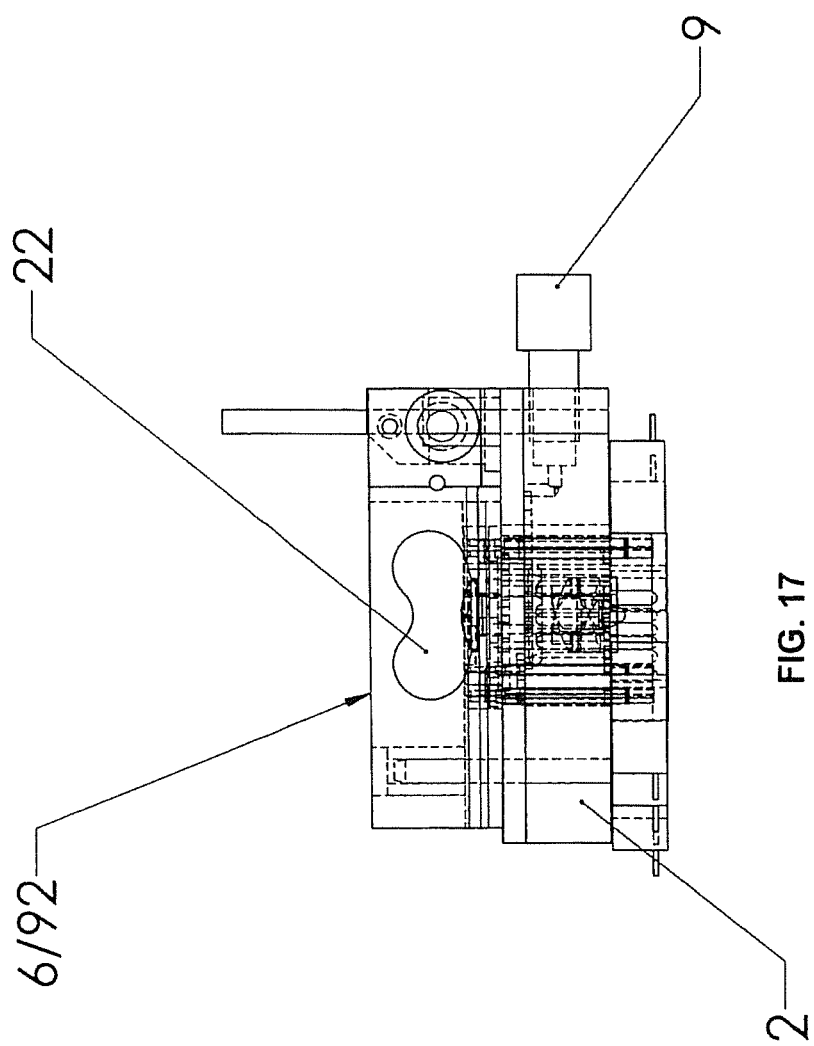

FIG. 17 is an end view of the particular embodiment of the microfluidic interface module shown in FIG. 14.

Figure 18:
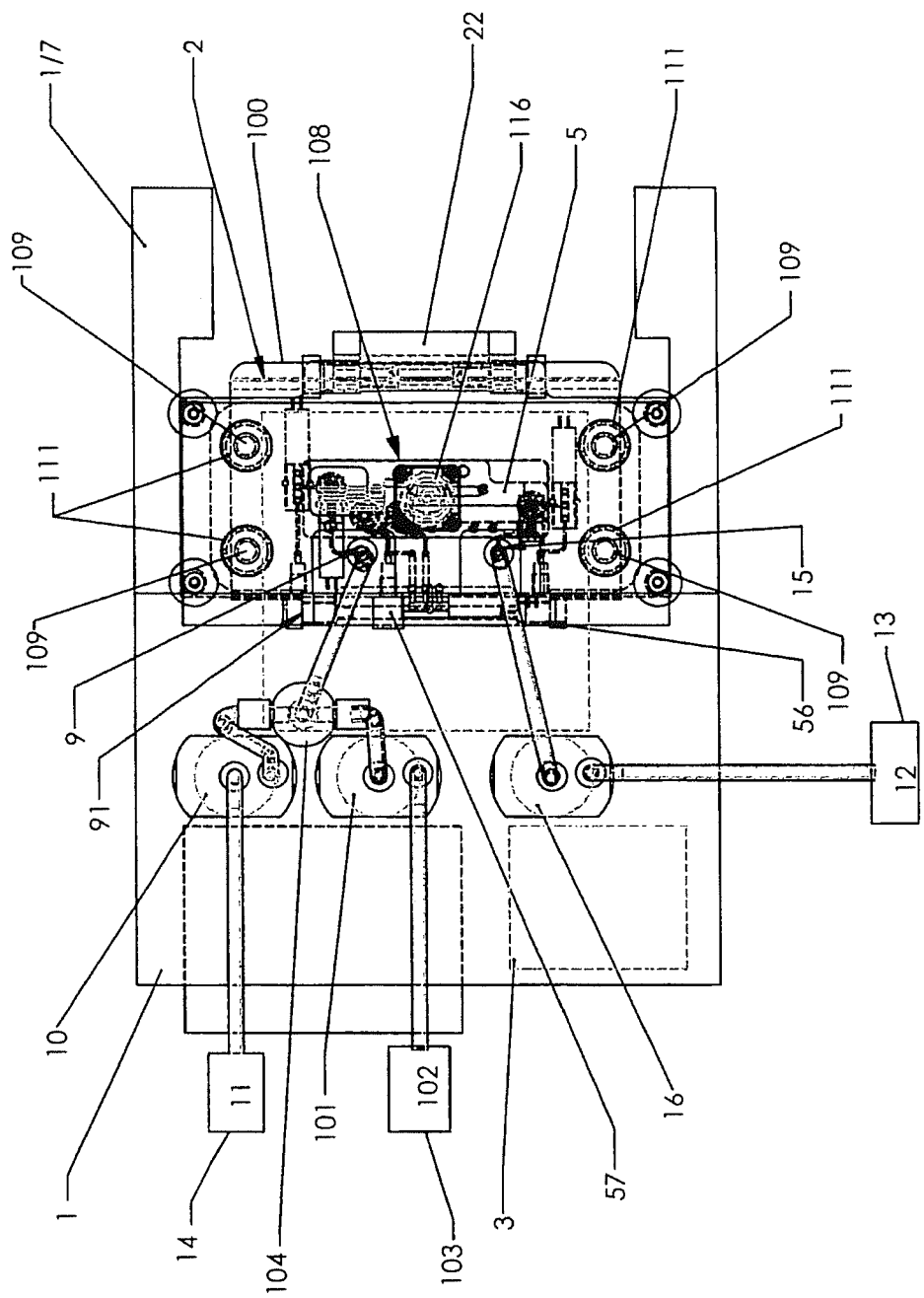

FIG. 18 is a top view of another particular embodiment of the invention.

Figure 19:
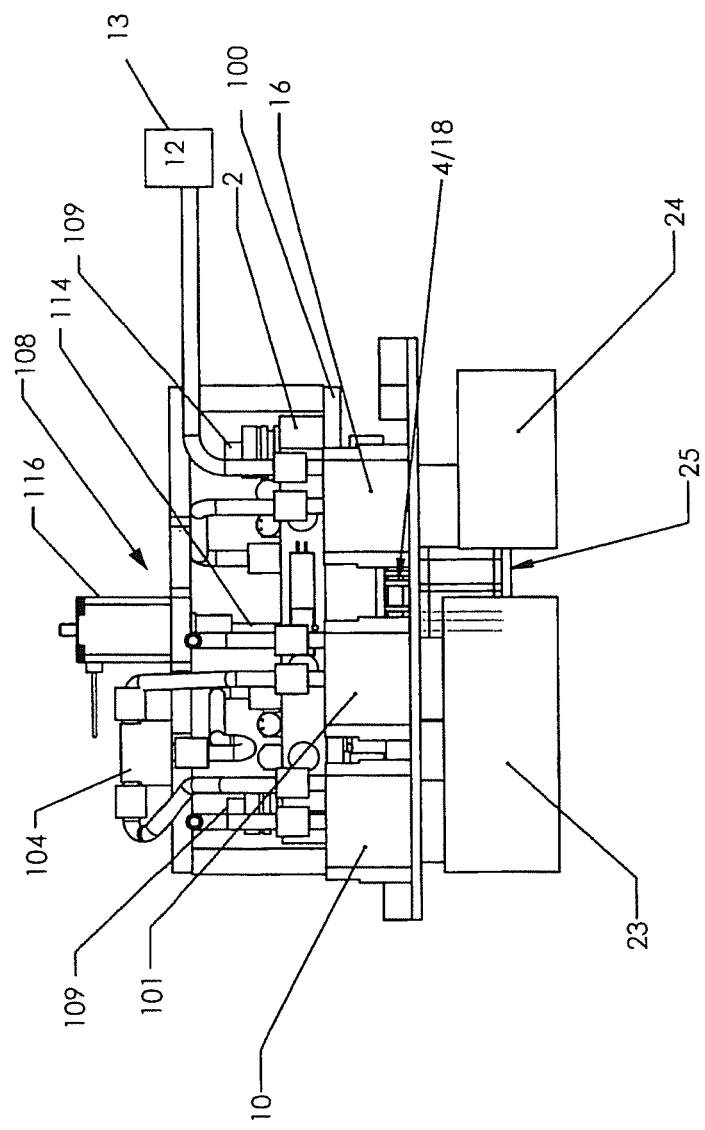

FIG. 19 is a front view of another particular embodiment of the invention.

Figure 20:
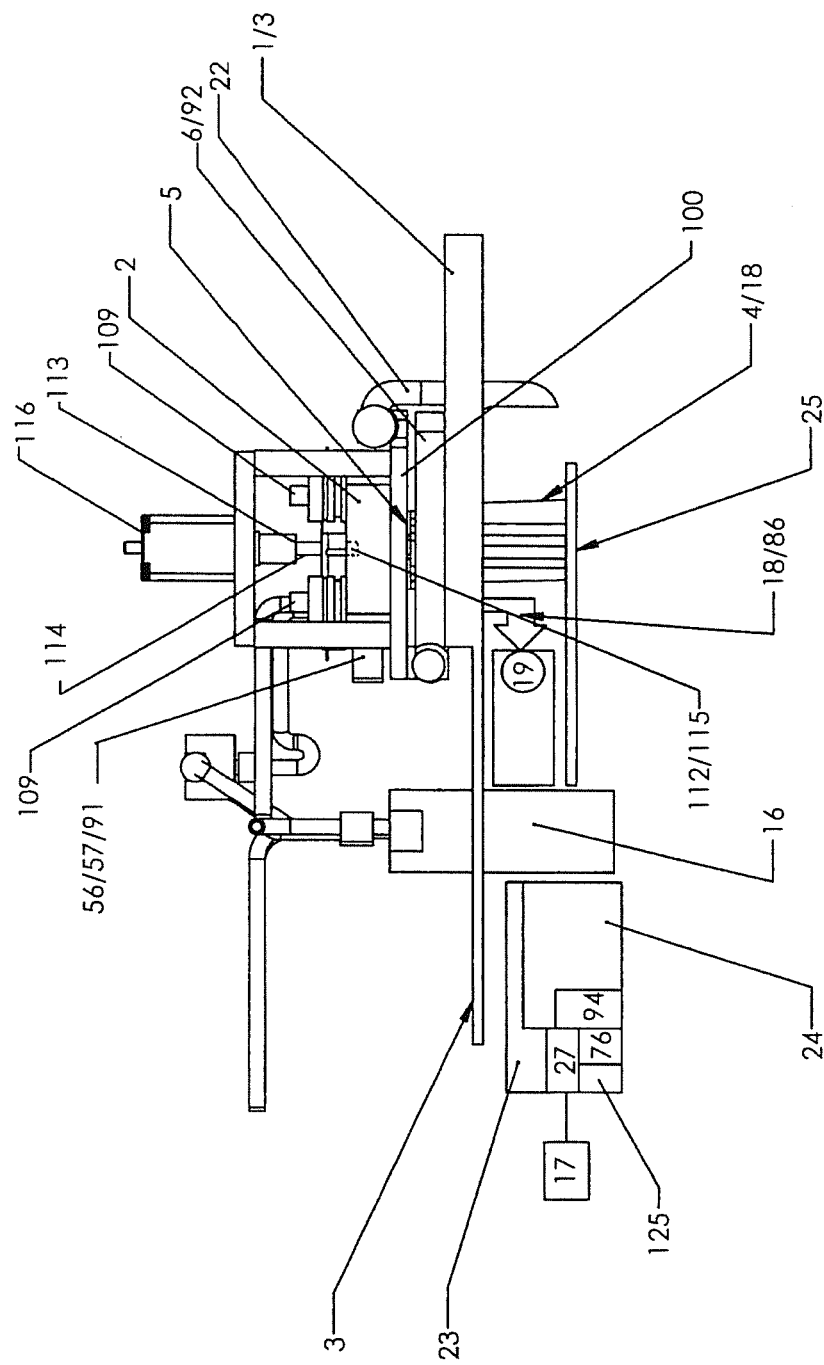

FIG. 20 is a side view of another particular embodiment of the invention.

Figure 21:
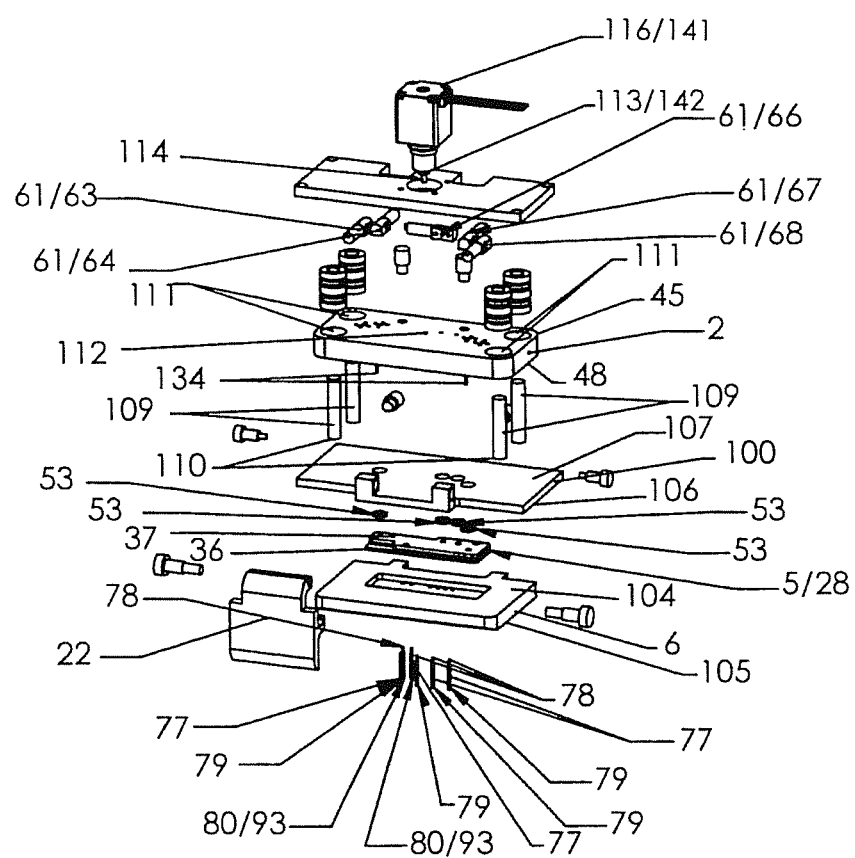

FIG. 21 is an exploded view of certain elements of the particular embodiment of the invention shown in FIGS. 18, 19, and 20.

Figure 22:
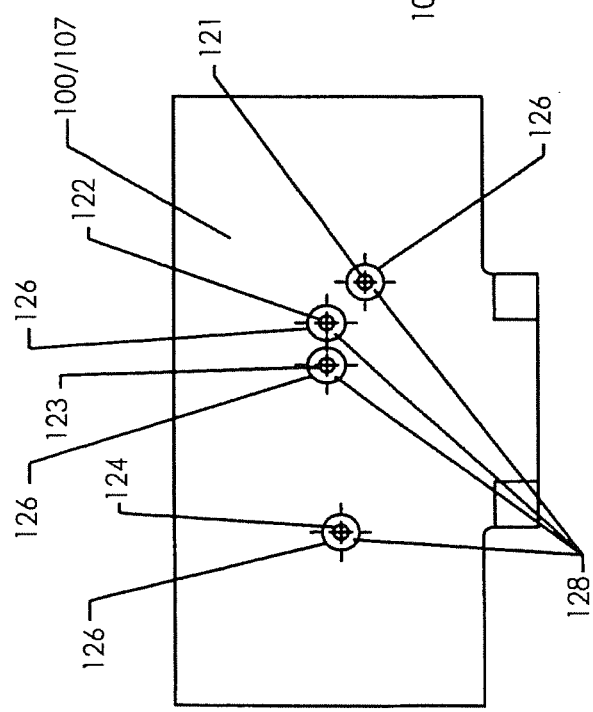

FIG. 22 is bottom view of a particular embodiment of a manifold having an outlet face which engages the second side of a particular embodiment of the microfluidic chip to sealably couple fluid inlet ports and fluid outlet ports with corresponding fluid inlets and fluid outlets on the second side of the microfluidic chip.

Figure 23:
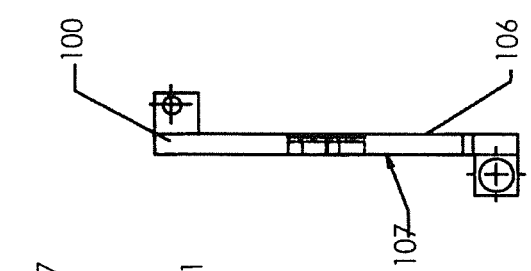

FIG. 23 is a side view of the particular embodiment of the manifold shown in FIG. 22.

Figure 24:
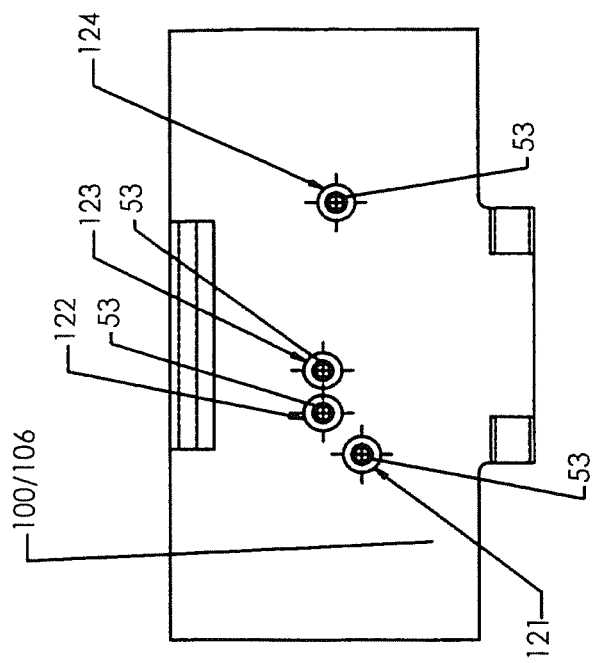

FIG. 24 is top view of the particular embodiment of a manifold shown in FIGS. 22 and 23 having an inlet face which engages the first side of a particular embodiment of the microfluidic interface module of second side of a particular embodiment of the microfluidic chip to sealably couple fluid inlet ports and fluid outlet ports of the manifold with corresponding supply ports and waste ports of the microfluidic interface module.

Figure 25:
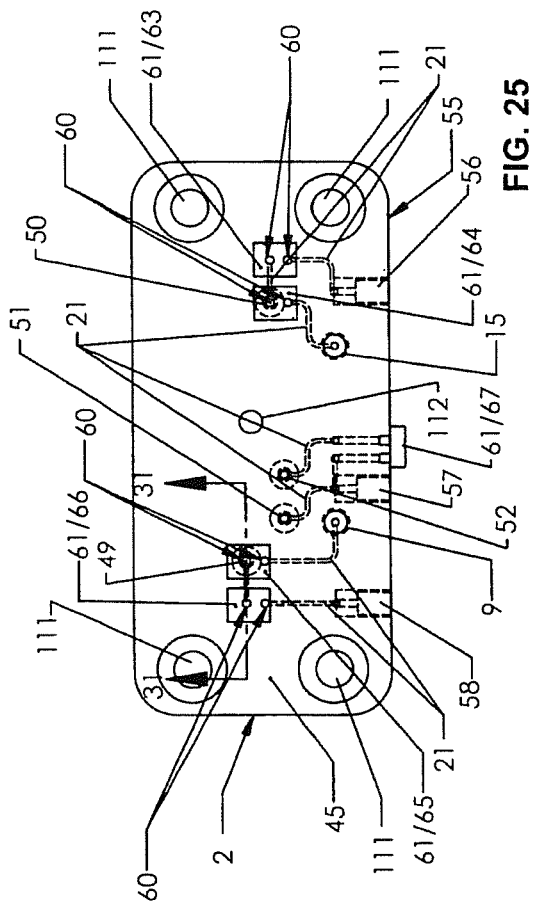

FIG. 25 is a side view of a particular embodiment of a microfluidic interface module which removably sealably engages the manifold shown in FIGS. 22, 23, and 24.

Figure 26:
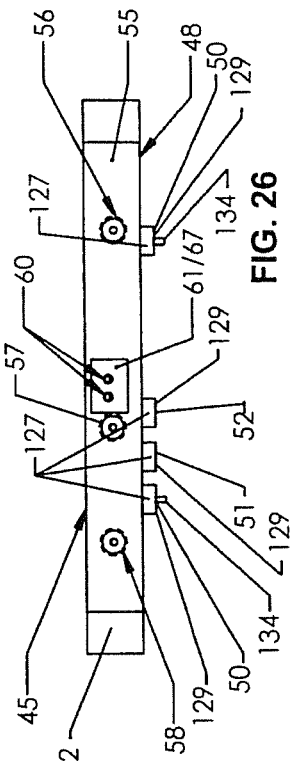

FIG. 26 is a top view of a particular embodiment of a microfluidic interface module which removably sealably engages the manifold shown in FIGS. 22, 23, and 24.

Figure 26A:
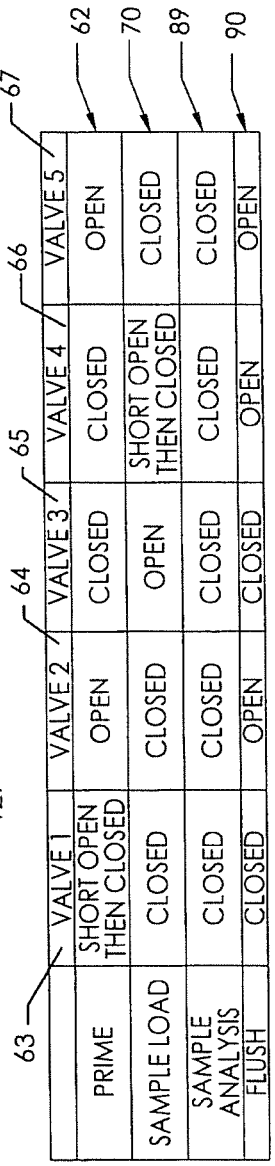

FIG. 26A is a table which provides the steps of a particular method of operating the embodiment of the microfluidic interface module shown in FIGS. 25 and 26.

FIG. 27 is a top view of a particular embodiment of a microfluidic capillary electrophoresis chip.

FIG. 28 is a side view of the particular embodiment of the microfluidic capillary electrophoresis chip shown in FIG. 27.

FIG. 29 is an end view of the particular embodiment of the microfluidic capillary electrophoresis chip shown in FIG. 27.

Figure 30:
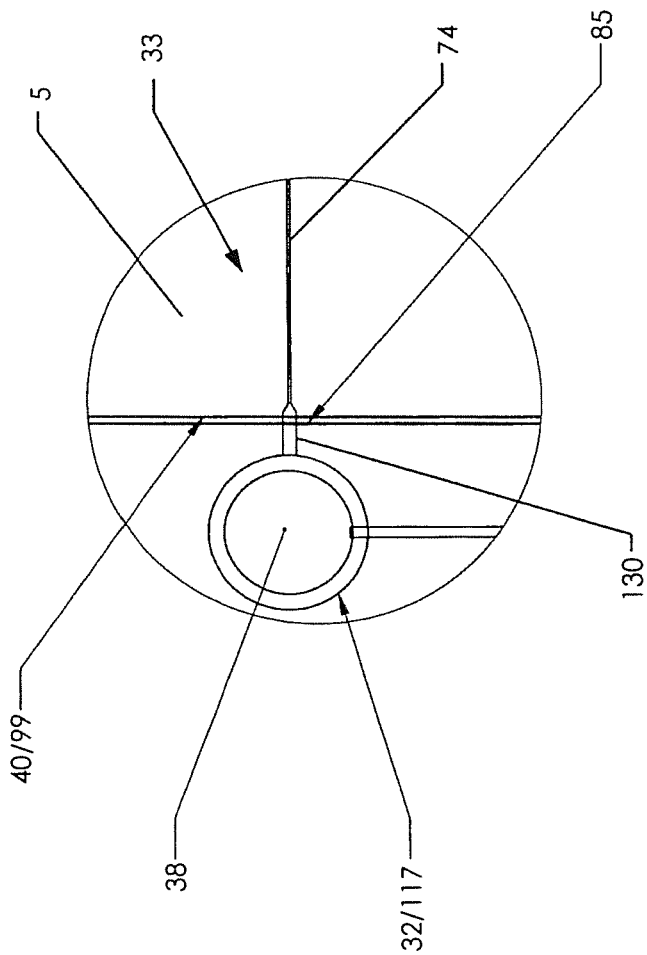

FIG. 30 is an enlarged view of a portion of the particular embodiment of the microfluidic capillary electrophoresis chip shown in FIG. 27.

Figure 31:
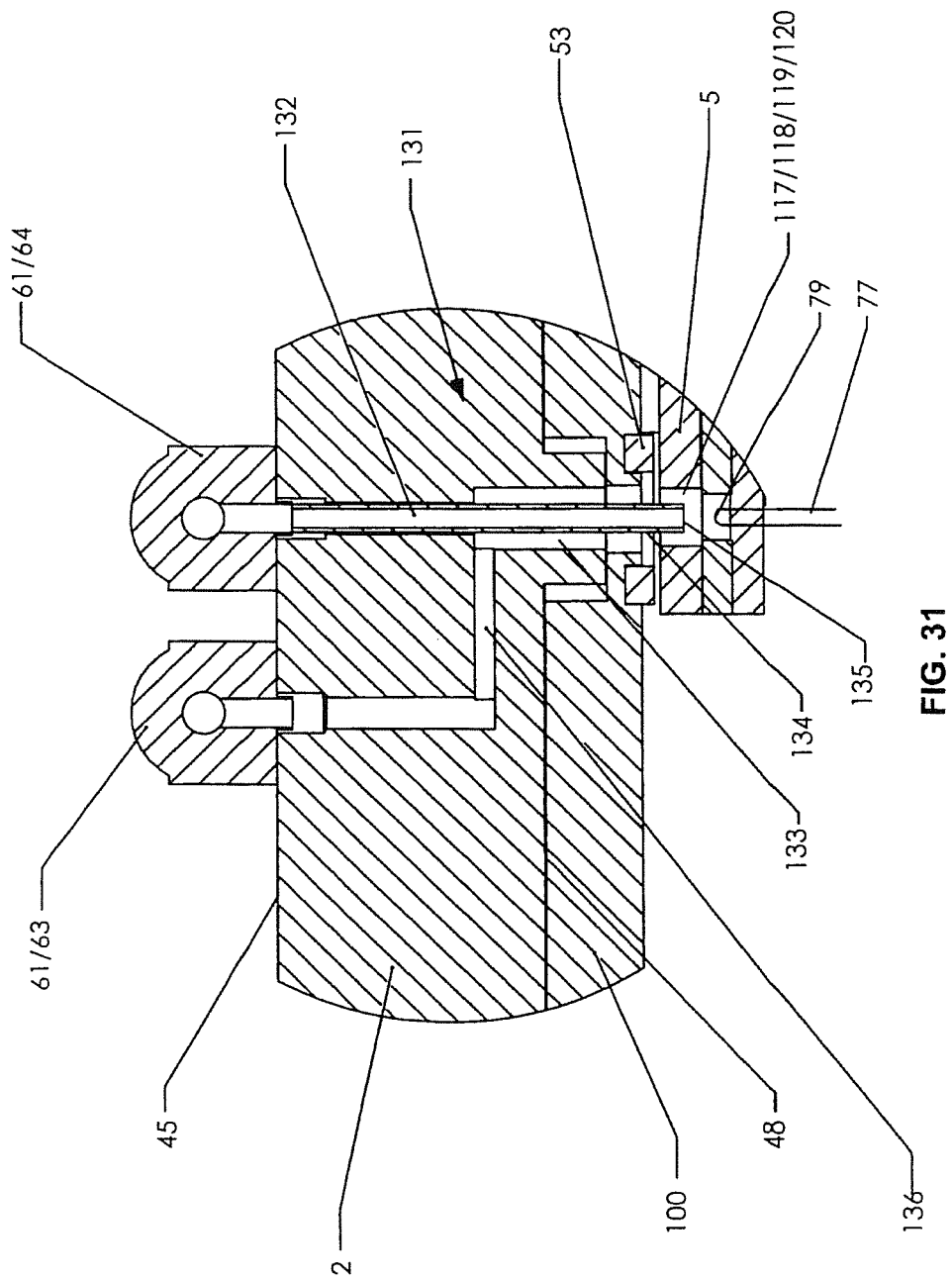

FIG. 31 is a cross section view 31-31 shown in FIG. 26 of the particular embodiment of a microfluidic interface module engaged to a corresponding portion of the manifold shown in FIG. 22 which is engaged with the corresponding portion of the microfluidic capillary electrophoresis chip shown in FIG. 27

Figure 32:
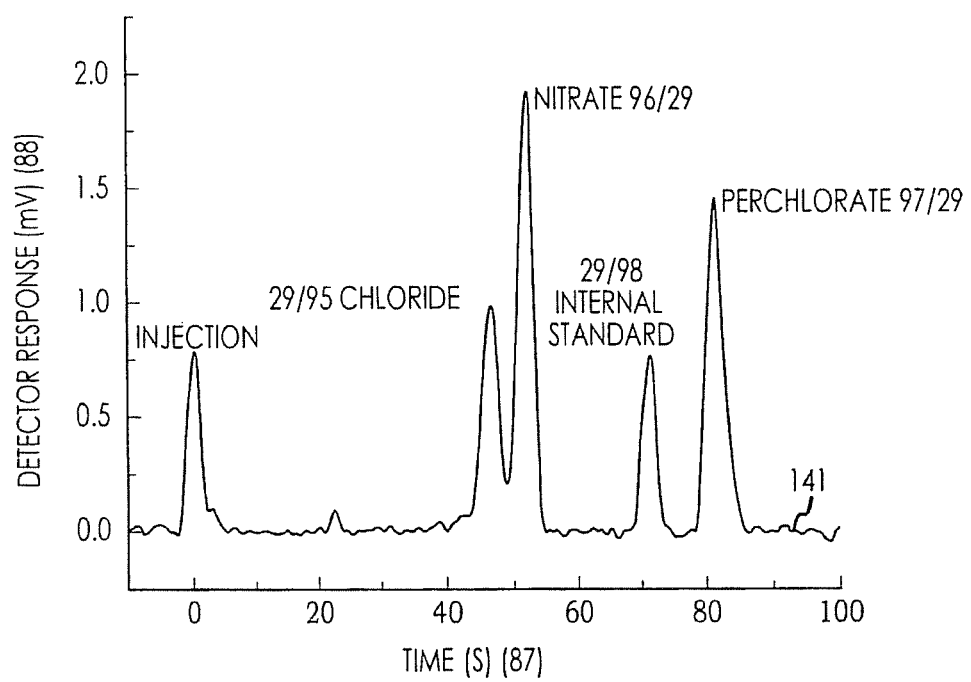

FIG. 32 is a chromatogram which shows the separation of substances within a sample fluid processed in accordance with the stepwise method of FIG. 12 B.

Figure 33:
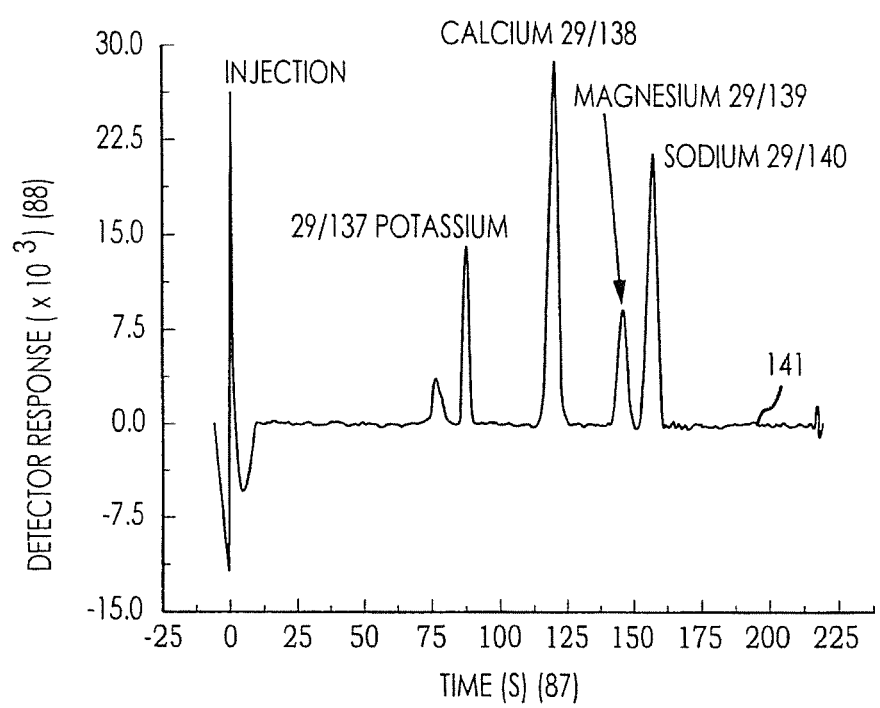

FIG. 33 is a chromatogram which shows the separation of substances within a sample fluid processed in accordance with the stepwise method of FIG. 26A.

V. MODE(S) FOR CARRYING OUT THE INVENTION

A capillary electrophoresis system which provides embodiments of a microfluidic chip for capillary electrophoresis and corresponding embodiments of a microfluidic interface module which fluidicly couples the microfluidic chip to external fluid sources and external repositories.

Now referring primarily to FIGS. 1-3, which provide a general overview of the relationship between a instrument housing (1) configured to receive and operably position: a microfluidic interface module (2), a fluid transfer assembly (3), an electrical interface (4), a microfluidic capillary electrophoresis chip (5) (also referred to as a "CE chip"), and a microfluidic chip enclosure (6). The embodiment of the support housing (1) as shown in FIG. 1 provides an external surface (7) with a recess element (8) configured to supportingly receive an embodiment of the microfluidic interface module (2) at a location which allows a sample supply port (9) to be fluidicly coupled to a sample transfer device (10) (such as a peristaltic pump, syringe pumps, reciprocating pumps, or like) which allows transfer of an amount of sample fluid (11) from a sample source (14) to the microfluidic interface (2) and which allows a carrier fluid supply port (15) to be fluidicly coupled to a carrier fluid transfer device (16)(such as a peristaltic pump, syringe pumps, reciprocating pumps, or like) which allows transfer an amount of carrier fluid (12) (electrically conductive fluids, electrically conductive liquid, analysis fluid, electrolyte, or the like, which allows separation of substances (29) based on size to charge ratio) from a carrier fluid source (13).

As further shown by FIGS. 1-3, embodiments of the support housing (1) can further receive the microfluidic interface module (2) at a location which allows the CE chip (5) to removably fluidicly engage the microfluidic interface module (2) to receive carrier fluid (12) and sample fluid (11) (or other fluids depending upon the application) for the separation, detection or analysis of substances (29) within the sample fluid (11) and to engage the electrical interface (4) to receive power from an external power source (17) and to couple electrical signals (18) from the CE chip (5) to external analysis electronics module (19). While the particular embodiment of the support housing (1) shown in FIGS. 1-3 provides a recess element (8) which receives the fluidic interface module (2), the invention is not so limited and embodiments of the support housing (1) can have numerous and varied configurations which act to locate the components of a corresponding numerous and varied embodiments of the invention in functional relation to operate as further described below.

The microfluidic chip enclosure (6) can operate between an open condition (20) (as shown in FIGS. 1-3) which allows removable engagement of the CE chip (5) with the microfluidic interface module (2) and a closed condition (92) (as shown in FIGS. 16-17) which sufficiently forcibly urges mated surfaces of the CE chip (5) and the microfluidic interface module (2) against each other to sealably fluidicly couple the network of microfluidic interface channels (21) (as shown for example in FIGS. 12A and 13A) disposed in the microfluidic interface module (2) with the network of channels in the CE chip (5) (as shown for example in FIGS. 12A and 13A), as further described below.

While FIGS. 1-3 show the microfluidic chip enclosure (6) rotatably coupled to the support housing (1) by the side; the invention is not so limited and the microfluidic chip enclosure (6) can be rotatably coupled to the support housing (1) by an end (or otherwise coupled to the support housing (1) to allow releasable sealable coupling with the CE chip (5)), or can be separate and manually located in relation to the support housing (1) or the CE chip (5), or the like. The microfluidic chip enclosure (6) can further provide mechanical fasteners (22) to fix the location of the microfluidic chip enclosure (6) in relation to the CE chip (5) and the microfluidic interface module (2) and to further maintain sufficient forcible engagement between the CE chip (5) and the microfluidic interface module (2) to maintain sealed fluidic coupling of the respective flow paths of the channels. While the mechanical fasteners (22) shown are spirally grooved and rotatably operate to act upon the microfluidic chip enclosure (6); the invention is not so limited, and any mechanical fastener (22) which can operate to sufficiently forcibly urge the microfluidic chip enclosure (6) against the CE chip (5) as above described may be suitable, including for example mated halves of a snap fastener, friction fitting, catch fastener, or the like. The support housing (1) can further define an enclosed space (23) for location of power regulation elements (24), an external analysis electronics module (19), computer processor (94), memory elements (26), and electrical circuitry (25) and other electronics that support or are otherwise associated with the particular method of capillary electrophoresis utilized and substance detection performed in the CE chip (5).

Figure 4:
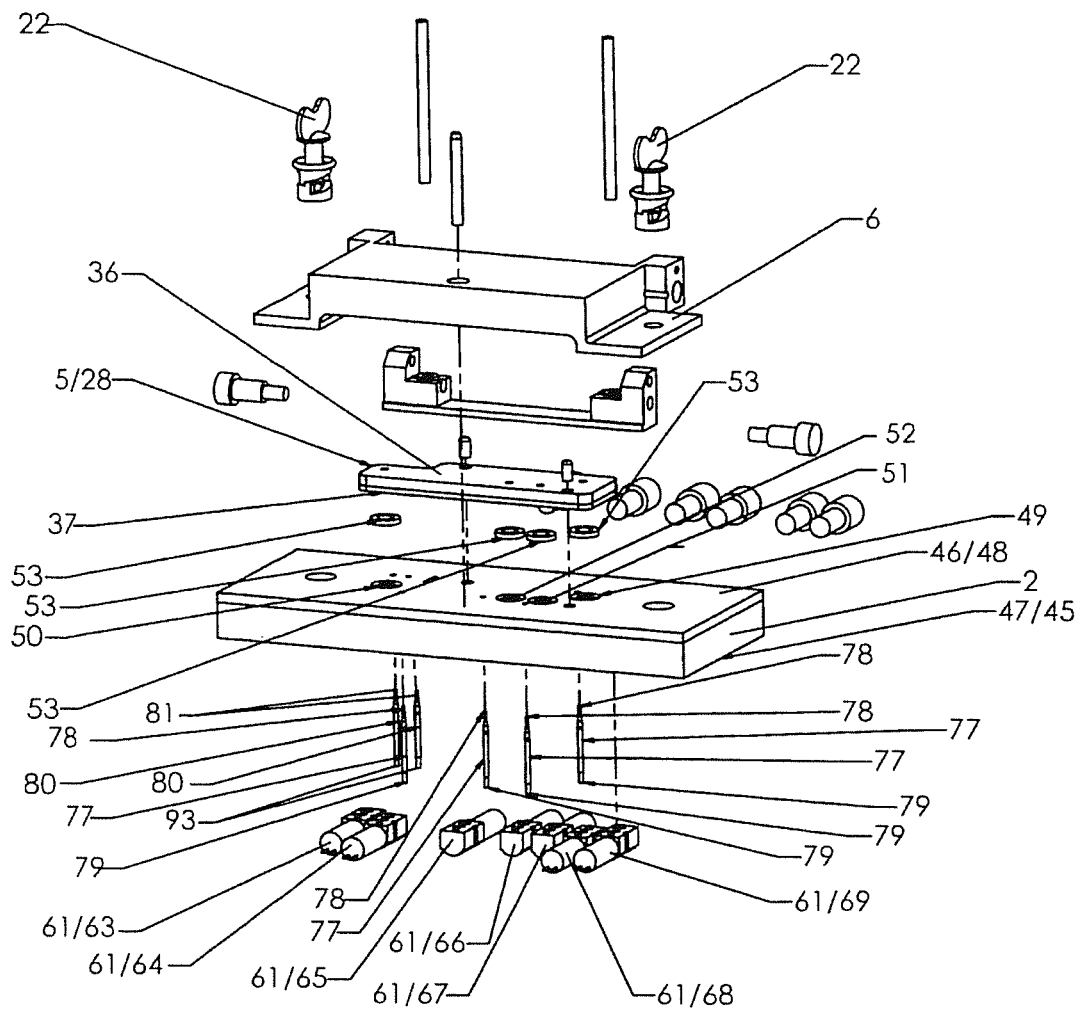
FIG. 4 is an exploded view of a particular embodiment of the invention.
Figure 5:
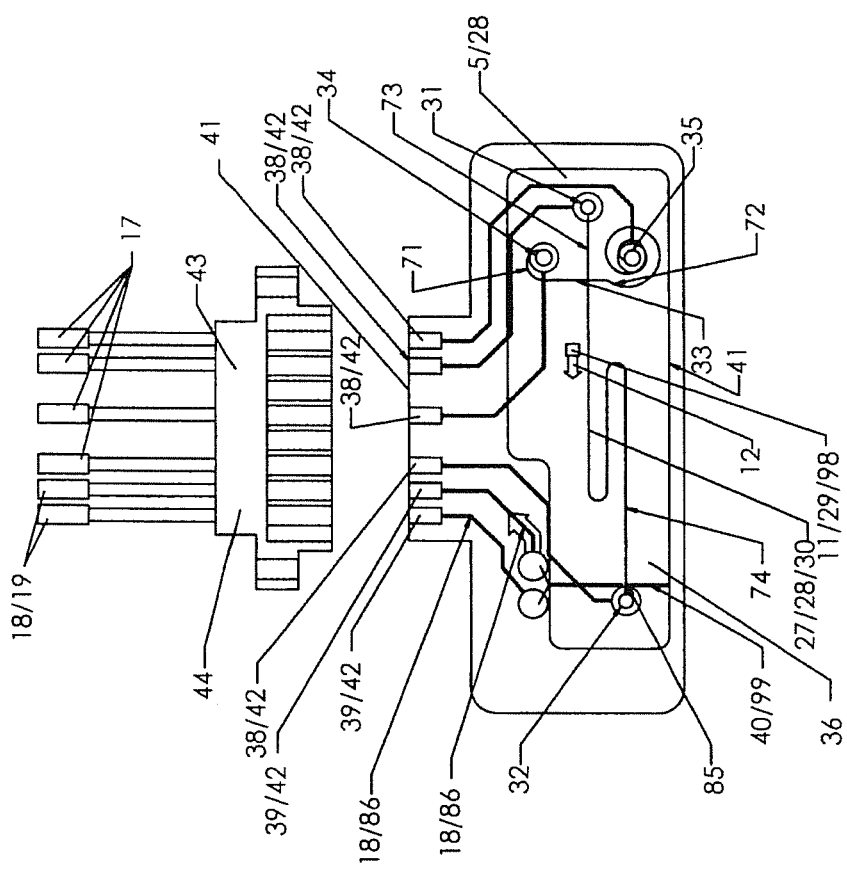
FIG. 5 is a top view of a particular embodiment of a microfluidic capillary electrophoresis chip.
Figure 6:
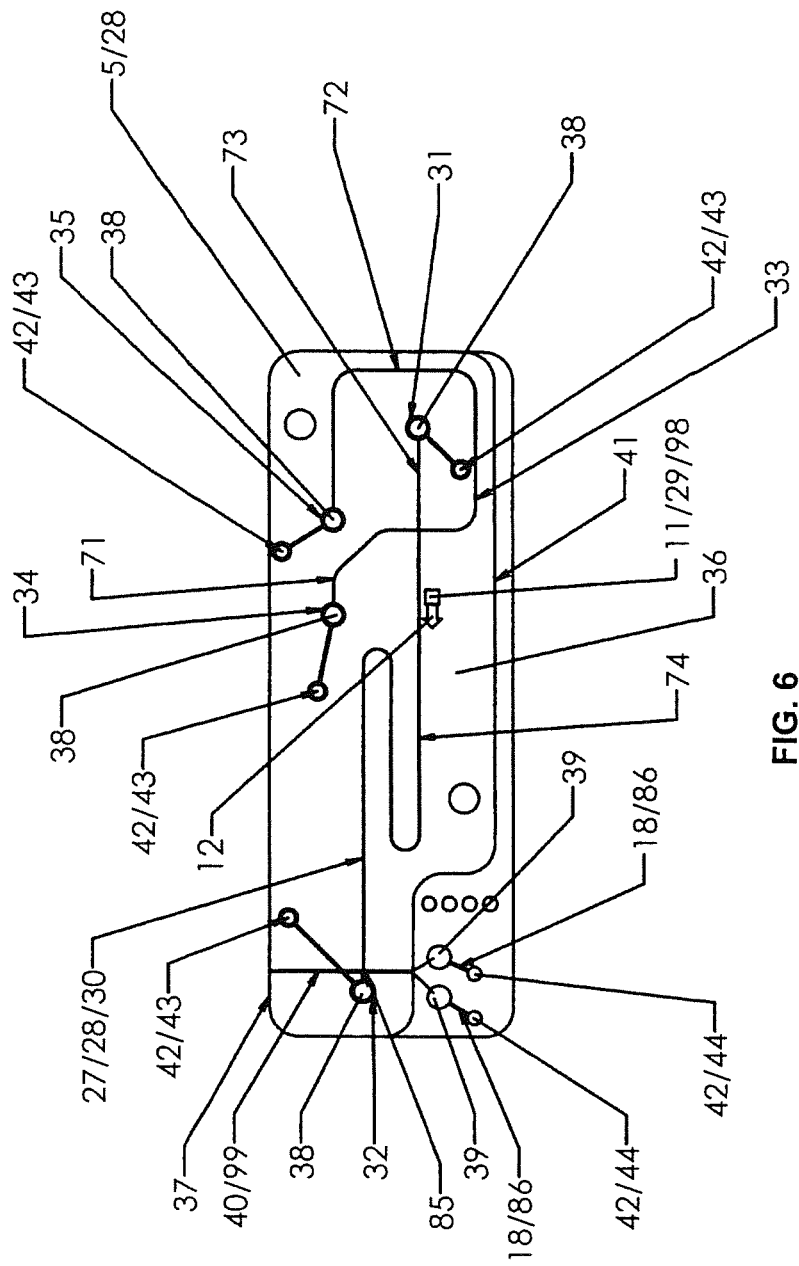
FIG. 6 is a top view of a particular embodiment of a microfluidic capillary electrophoresis chip.

Now referring primarily to FIGS. 4-6, which provides an exploded view of a particular embodiment of the CE chip (5) and the microfluidic interface module (2) and the microfluidic chip enclosure (6) and FIGS. 5 and 6 which show two non-limiting embodiments of a CE chip (5), embodiments of the CE chip (5) can have one or more capillary electrophoresis channel(s) (27) ("CE channel(s)") disposed in a substrate material (28) (see for example FIGS. 5 and 6). CE chips (5) can be produced from a substrate material (28) compatible with the sample fluids (11) and carrier fluids (12) or other fluids flowed in the CE channels (27) and the methods of capillary electrophoresis to be performed in the CE channels (27) in relation to such fluids. Non-limiting examples of suitable substrate materials include: a polymeric material, such as polycarbonate, polymethylmethacrylate (PMMA), cylco-olefin-copolymer (COC), glass, metal, or the like. The substrate material (28) can be provided as one layer or a plurality of layers depending on the manner of fabrication of the CE chip (5) or the fabrication of the CE channel(s) (27) disposed therein. Embodiments of the CE chip (5) can have external dimensions sufficient to dispose the CE channel(s)(27) in the substrate material (28) and sufficient to provide an external surface configuration suitable for engagement with the microfluidic interface module (2) and microfluidic chip enclosure (6).

The term "CE channel" as used herein refers to a pathway(s) formed in or through the substrate material (28) of a CE chip (5) that allows for movement of carrier fluid (12) or sample fluid (11) (or other fluids depending upon the application) within selectably variable embodiments of the CE channel (27), as further described below, and in which electrophoretic separation of substances (29) or detection of substances (29) by electrochemical, voltammetry, or optical means can be performed. Non-limiting embodiments of the CE channel (27) can provide a carrier channel (30) having a length disposed between a sample inlet (31) and a carrier fluid inlet (32). The length of the carrier channel (30) can be in the range of about 1 cm to about 20 cm long with embodiments varying in increments of about 0.5 cm within the range, depending upon the application and having a generally rectangular cross-section having a width in the range of about 10 microns to about 200 microns with embodiments varying in increments of 2 microns within the range and a height in the range of about 5 microns to about 200 microns with embodiments varying in increments of 2 microns within the range.

One or more cross channel(s) (33) having a length disposed between a cross channel inlet (34) and a cross channel outlet (35) can intersect the carrier channel (30). Depending on the configuration of the CE chip (5) the cross channel inlet (34) can be located on one side of the carrier channel (30) and the cross channel outlet (35) can be located on the opposite side of the carrier channel (30)(see for example FIG. 5) or as to certain embodiments, the cross channel inlet (34) and the cross channel outlet (35) can be located on the same side of the carrier channel (30) (see for example FIG. 6) even though the cross channel (33) intersects the carrier channel (30). The length of the cross channel (33) between the cross channel inlet (34) and the carrier channel (30) can be in the range of about 0.5 cm to about 15 cm (this portion of the cross channel (33) also referred to as the "first cross channel leg" (71)) and the length of the cross channel (33) between the cross channel outlet (35) and the carrier channel (30) can be in the range of about 0.5 cm to about 15 cm (this portion also referred to as the "second cross channel leg" (72)) with embodiments varying in increments of 0.5 cm within the range and having a generally rectangular cross-section having a width in the range of about 10 microns to about 200 microns and a height in the range of about 5 microns and about 200 microns with embodiments varying in increments of 2 microns within the range. However, these particular examples are not intended to be limiting, and configurations of the CE channel (27) can be of any length and cross-sectional configuration suitable for use in a microfluidic CE chip (5). While FIGS. 5 and 6 show the cross channel (33) intersecting with the carrier channel (30) in generally perpendicular relation and the first cross channel leg (71) and the second cross channel leg (72) in 180° relation; the invention is not so limited, and the cross channel (33) can intersect the carrier channel (30) at different angles and the first cross channel leg (71) and the second cross channel leg (72) can be disposed at angles other than 180°. Additionally, the term "intersect" includes those embodiments of the cross channel (33) in which the first leg (71) and the second leg (72) intersect the carrier channel (30) offset a distance from each other along the length of the carrier channel (30).

Intersection of the cross channel (33) with the carrier channel (30) can define two regions of the carrier channel (30). A first disposed between the sample inlet (31) and the intersection of the cross channel (33) referred to as the "sample leg" (73) and a second disposed between the carrier fluid inlet (32) and the intersection of the cross channel (33) referred to as the "separation leg" (74). The carrier fluid inlet (32) and the sample fluid inlet (31) and the cross channel inlet (34) and the cross channel outlet (35) can all communicate with one of two opposed generally planar parallel faces (36)(37) of the CE chip (5) without otherwise altering the generally planar faces (36)(37) of the CE chip (5).

Embodiments of the CE chip (5) can further provide a first electrical circuit (38) whether as an imprinted circuit or hard wires) on the first face (36) or the second face (37) of the CE chip (5) which couples power from an external power source (17) to the CE chip (5). The first electrical circuit (38) can provide a voltage in the range of few hundred volts and sometimes above one thousand volts (also referred to as "high voltage") conducted through the carrier fluid (12) in the carrier channel (30) typically between the cross channel inlet (34) and the carrier fluid inlet (32) sufficient to induce an electro-osmotic flow in the separation leg (74) for separation of various charged substances (29) in a small amount of sample fluid (11). The first electrical circuit (38) can further provide a voltage in the range of few hundred volts and sometimes thousand volts conducted through the sample fluid (11) typically within legs (72) and (73) and between sample inlet (31) and cross channel outlet (35) sufficient to induce an electro-osmotic flow of sample fluid (11). Timed adjustments in voltages applied to inlets (31, 34, and 35) can result in a small amount of sample fluid (11) being located at the start of the separation leg (74). Timed adjustments typically last from about 0.5 seconds to about 30 second in increments of 0.5 seconds within the range. Substances (29) in the small volume of sample fluid (12) separate as they migrate within separation leg (74).

A second electrical circuit (39) (whether as an imprinted circuit or hard wires) can provide power to a detection element (40) or couple electrical signals (18) from the CE chip (5) to external analysis electronics module (19), or both. The second electrical circuit (39) can include a detection element (40) consistent with the optical detection, amperometeric detection, electrical detection, voltametric detection, conductivity detection, or other method of detection of substances (29) within the sample fluid (11). The CE chip (5) can have a perimeter (41) configured to removably couple the electrical terminals (42) of the first electrical circuit (38) and the second electric circuit (39) with a corresponding first electrical interface (43) at one side of the CE chip (5) to provide external power (17) and a second electrical interface (44) which conveys electrical signals (18) from the detection elements (40) of the CE chip (5) to analysis electronics module (19) as shown for example in FIG. 5. Alternately, embodiments of the CE chip can have the electrical terminals (42) for the first electrical circuit (38) and the second electrical circuit (39) disposed on a face (36)(37) of the CE chip (5) to removably engage the first electrical interface (43) and the second electrical interface (44) disposed on the first microfluidic interface module face (48), as further described below.

Embodiments of the CE chip (5) removably received by the first electrical interface (43) and the second electrical interface (44) further engage the microfluidic interface module (2) to position the sample fluid inlet (31), the carrier fluid inlet (32), the cross channel inlet (34), and the cross channel outlet (35) at a location which allows sealable fluidic coupling of the CE chip (5) with the corresponding channels (21) of the microfluidic interface module (2) allowing control of the ingress and egress of carrier fluid (12) and sample fluid (11) (or other fluids depending upon the application) through the inlets and outlets of the CE chip (5).

Now referring primarily to FIG. 4 which shows an exploded view of a particular embodiment of the CE chip (5) as shown in FIG. 5 and a corresponding particular embodiment of the microfluidic interface module (2) which can take the constructional form of a first microfluidic interface layer (46) as shown in FIGS. 7-9 and a second microfluidic interface layer (47) as shown in FIGS. 10-11. The first microfluidic interface layer (46) can have a first module face (48) at which a sample port (49) and a carrier fluid port (50) communicate in dimensional relation for mated fluidic coupling with the corresponding sample inlet (31) and carrier fluid inlet (32) of the embodiment of the CE chip (5) shown in FIG. 5 and at which a cross channel outlet port (51) and a cross channel inlet port (52) communicate in dimensional relation for mated fluidic coupling with the corresponding cross channel outlet (35) and cross channel inlet (34) on the CE chip (5) shown in FIG. 5. The first module face (48) of the first microfluidic interface layer (46) can also be configured to receive a seal element (53) which surrounds each port (49)(50)(51)(52) which upon mated engagement of a chip face (36)(37) of the CE chip (5) with the first module face (48) of the first microfluidic interface layer (46) fluidically seals the inlet and outlet ports (49)(50)(51)(52) with corresponding inlets and outlets (31)(32)(34)(35) of the CE chip (5).

Now referring primarily to FIGS. 8-9 and 10-11, the second face (54) of the first microfluidic interface layer (46) can provide a first set of open sided channels (21a) and the first face (59) of the second microfluidic interface layer (47) can provide second set of open sided channels (21b) which can be closed by mated engagement of the second face (54) of the first microfluidic interface layer (46) with the first face (59) of the second microfluidic interface layer (47) to provide the network of microfluidic interface channels (21) (see for example FIG. 12A) within the microfluidic interface module (2). The assembled microfluidic interface module provides an external surface including a first module face (48) of first interface layer (46) which engages the CE chip (5) and an opposed second module face (45) of the second microfluidic interface layer (47) to which microfluidic valves (61) can be disposed, as further described below, and module sides (55).

Certain of the microfluidic interface channels (21) terminate at the a module side (55) (which can as to certain embodiments the side of the second microfluidic interface layer (47)) in communication with the sample supply port (9), the carrier fluid supply port (15), a first waste port (56), a second waste port (57), and a third waste port (58) and a fourth waste port (91) for ingress and egress of sample fluid (11) and carrier fluid (12) (or other fluids depending upon the application) to and from the microfluidic interface channels (21). A lesser or greater number of supply ports or waste ports can be utilized depending upon the embodiment.

Again referring primarily to FIGS. 10 and 11, the second microfluidic interface layer (47) can further provide one or more pairs of bores (60) which communicate between the second module face (45) of the microfluidic interface module (2) to intersect corresponding pairs of microfluidic interface channels (21) within the microfluidic interface module (2). Now referring primarily to FIGS. 12A and 15, one or more pair of bores (60) can be disposed at the second module face (45) of the microfluidic interface module (2) in dimensional relation which allows each of the pairs of bores (60) to be fluidicly coupled through a microfluidic valve (61) (also referred to as a "valve") coupled to the second module face (45) of the micofludic interface module (2). A non-limiting example of a microfluidic valve (61) suitable for use with embodiments of the microfluidic interface module (2) can be obtained from The Lee Company, Part No. LHDA 0521111; however, the invention is not so limited and any valve which allows interruptible fluidic coupling of a pair of bores as below described may be utilized.

Figures 12A, 12B:
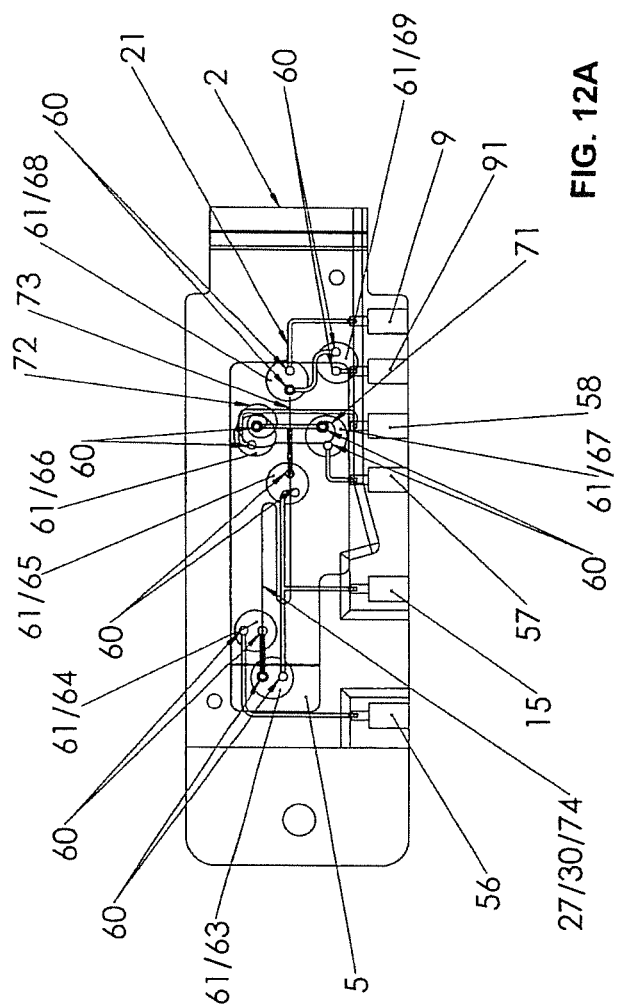
FIG. 12A is a top view of a first side of a particular embodiment of the microfluidic interface module engaged to the microfluidic capillary electrophoresis chip of FIG. 5.
FIG. 12B is a table which provides the steps of a particular method of operating the embodiment of the microfluidic interface module shown in FIG. 12A engaged to the microfluidic capillary electrophoresis chip of FIG. 5.

Now referring primarily to FIG. 12A, which shows a particular embodiment of the microfluidic interface module (2) which fluidicly couples the particular embodiment of the CE chip (5) shown in FIG. 5, each one of the microfluidic valves (61) can operate between a closed condition which interrupts fluid flow between a pair of bores (60) and an open condition which allows fluid flow between a pair of bores (60). The valves (61) can each be activated or driven between the closed condition and the open condition based on an event schedule (75) to correspondingly alter the configuration of the flow paths within the network of microfluidic interface channels (21) to carry out each of a plurality steps (as non-limiting examples, steps (62)(70)(89)(90) shown in FIG. 12B or 13B) of a method for use of embodiments of the microfluidic interface module (2) to process an amount of sample fluid (11) within a fluidicly coupled CE chip (5). The event schedule (75) can be implemented by a computer processor (94) which operates in accordance with the executable instructions of an event schedule computer program (76) to match the open condition and the closed condition of each valve (61) against a time schedule to provide one or more configurations of the flow paths within the network of microfluidic interface channels (21) of the microfluidic interface module (2) to carry out each of the plurality of steps in an event schedule (75).

Now referring primarily to FIG. 12B which provides a non-limiting embodiment of an event schedule (75) including the steps of a method for use of the particular embodiment of the microfluidic interface module (2) shown in 12A fluidicly coupled to the particular embodiment of the CE chip (5) of FIG. 5 to process an amount of sample fluid (11). In a step of priming (62) the CE chip (5) prior to introduction of an amount of sample fluid (11), valve 2 (64), valve 4 (66), valve 5 (67), and valve 7 (69) can be established in the open condition. Valve 3 (65) can then established in the open condition to allow ingress of carrier fluid (12) from the carrier fluid supply port (15) through valve 3 (65), valve 4 (66) and valve 5 (67) to deliver carrier fluid (12) to the cross channel inlet (34) and cross channel outlet (35) of the CE chip (5). Opening valve 1 (63) for a short duration allows carrier fluid (12) to flow within separation leg (74) of the carrier channel (30) and the sample leg (73) of the carrier channel (30) to the first waste port (56), the second waste port (57), and the third waste port (58). This step establishes the CE chip (5) in condition to receive an amount of sample fluid (11).

The event schedule (75) further includes the step of sample loading (70). The step of sample loading (70) includes establishing valve 4 (66), valve 5 (67) and valve 6 (68) in the open condition to deliver an amount of sample fluid (11) from the sample supply port (9) of the microfluidic interface module (2) to fill the sample inlet (31) of the CE chip (5) (as to certain embodiments a portion of the sample leg (73) of the carrier channel (30).

Now referring primarily to FIG. 5, which shows an embodiment of the CE chip having a first electrical interface (43) and a second electrical interface (44) in the form of a ribbon connector which insertingly accepts electrical terminals (42) imprinted on a part of a circuit board, the first electrical interface (43) couples an external power source (17) to the first electrical circuit (38) imprinted on the CE chip (5) to generate a flow of current in the electrically conductive buffer solution (carrier fluid) (12) within the carrier channel (30) of the CE chip (5) fluidicly engaged to the microfluidic interface module (2). All of the valves (61) of the microfluidic interface module (2) can be established in the closed condition as the various charged substances (29) within the sample fluid (11) loaded within the sample leg (73), as above described, becomes differentially mobile within the separation leg (74) upon application of sufficient voltage. The differences in electrophoretic mobility can result in separation of different charged substances (29) within the separation leg (74).

The second electrical circuit (39) of the CE chip (5) couples electrical signals (18) from a detection element (40) with external analysis electronics module (19). The detection element (40) can be directly or indirectly coupled to the separated substances (29) moving within the separation leg (74) at a detection location (85). The second electrical circuit (39) can be configured to support any of a variety of detection elements (40), such as: amperometric sensors, conductivity sensors, voltametric sensors, optical sensors, or the like. During the step of sample fluid analysis (89), the detection element (40) can generate a detection signal (86) which varies based upon the differences in optical characteristics, electrochemical characteristics or electrical characteristics of each separated substance (29) at the detection location (85) within the separation leg (74). Accordingly, as separated substances pass through the detection location (85) of the separation leg (74) the detection element(s) (40) generate a detection signal (86) which varies based upon one or more characteristics of a substance (29). A standard or a mixture of standards for each substance (29) to be determined by capillary electrophoresis can be run under controlled conditions in the desired configuration of a CE channel (27) to produce CE channel standard data (125) against which substances (29) in a sample fluid (11) can be compared in terms of electrophoretic mobility (87) (period of time to detection) and detection signal amplitude (88) (see FIGS. 32 and 33) such that substances (29) in each amount of sample fluid (11) separated in the CE chip (5) can be identified and the concentration of the substance (29) in a sample fluid (11) determined by the functionalities of the external analysis electronics module (19). Additionally, an internal standard (98) can be mixed into a sample fluid (11) at a known concentration to be used as a reference to quantify a compound of interest at an unknown concentration, also referred to as an internal standard (98).

Again referring to FIGS. 12 A, 12B and 5, the inventive method can further include the step of flushing (90) the CE chip (5) after the step of sample fluid analysis (89). As shown in FIG. 12B the flushing (90) step can be achieved by opening valve 1 (63), valve 4 (66), valve 5 (67), and valve 7 (69) to allow carrier fluid (12) to be delivered through the separation leg (74) and through the first and second cross channel legs (71) (72) to the cross channel inlet (34) and the cross channel outlet (35) and the sample leg (73) to the sample inlet (31) which allows egress of the carrier fluid (12)

from the first waste port (56), the second waste port (57) and the third waste port (58) of the microfluidic interface module (2). The steps in the method can be repeated to automatically run a plurality of fluid samples (11) in serial order from one or a plurality of different sample sources (14).

Figures 13A, 13B:
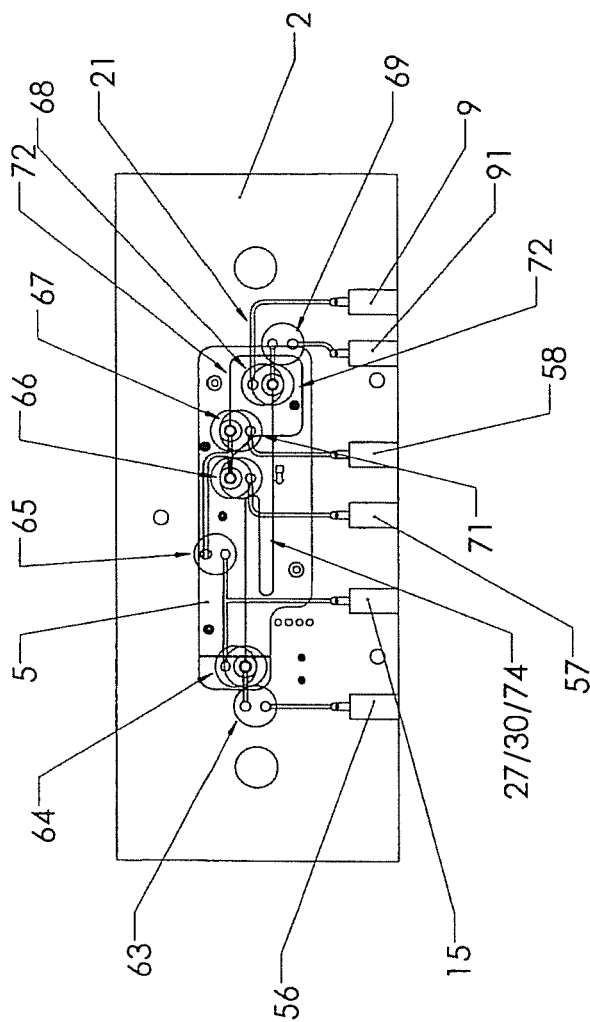
FIG. 13A is a top view of a first side of a particular embodiment of the microfluidic interface module engaged to the particular embodiment of the microfluidic capillary electrophoresis chip of FIG. 6.
FIG. 13B is a table which provides the steps of a particular method of operating the embodiment of the microfluidic interface module shown in FIG. 15A engaged to the microfluidic capillary electrophoresis chip of FIG. 6.

Now referring primarily to FIGS. 4, 13A and FIG. 6, which shows an alternate embodiment of the microfluidic interface module (2) fluidicly coupled to the CE chip (5) of FIG. 6. While the steps in the method of using the microfluidic interface module (2) fluidicly coupled with CE chip (5) of FIG. 6 including the steps of: priming (62), sample loading (70), sample fluid analysis (89), and sample flushing (90) of the CE chip (5) remain substantially unchanged and controlled by operation of a plurality of valves (61) generally as above-described, the constructional form of the microfluidic interface module (2) provides an alternative embodiment of the first electrical interface (43) and the second electrical interface (44) with the CE chip (5) of FIG. 6.

Now referring primarily to FIG. 4, one or more high voltage pins (77) can communicate between opposed sides (45)(48) of the microfluidic interface module (2) to provide a corresponding one or more first high voltage pin ends (78) which extend outwardly from first surface (48) of the microfluidic interface module (2) a sufficient distance to electrically couple a corresponding terminal (42) of the first circuit (38) of the CE chip (5) upon mated engagement with the microfluidic interface module (2). The one or more high voltage pins (77) can further provide one or more high voltage second pin ends (79) which extend outwardly from the second surface (45) of the microfluidic interface module (2). The second pin ends (79) can be coupled with the first electrical interface (43) to electrically couple an external power source (17) to the microfluidic interface module (2). All of the valves (61) can be established in the closed condition while voltage supplied at the first electrical interface (43) to one or more of the high voltage pins (77) generates a flow of current within the corresponding first circuit (38) of the CE chip (5) including the carrier fluid (12) (electrically conductive buffer) within the carrier channel (30). The various charged substances (29) within the sample fluid (11) loaded within the sample leg (73), as above described, can become differentially mobile within the separation leg (74) upon application of the voltage. The differences in electrophoretic mobility can result in separation of different charged substances (29) within the separation leg (74).

Again referring primarily to FIGS. 4 and 6, one or more detection pins (80) can communicate between opposed faces (45)(48) of the microfluidic interface module (2) to provide a corresponding one or more first detection pin ends (81) which extend outwardly from the first module face (48) of the microfluidic interface module (2) a sufficient distance to electrically couple the second electrical circuit (39) of the CE chip (5) upon mated engagement of the CE chip (5) with the microfluidic interface module (2). The one or more detection pins (80) can correspondingly provide one or more second detection pin ends (93) which extend outwardly from the second module face (45) of the microfluidic interface module (2) to electrically couple the second electrical interface (44) with external analysis electronics module (19) of a computer (94). The second electrical circuit (39) of the CE chip (5) includes a detection element (40) which can be directly or indirectly coupled to the separated substances (29) moving within the separation leg (74) at a detection location (85). The second electrical circuit (39) can be configured to support any of a variety of detection elements (40), such as: amperometric sensors, conductivity sensors, voltametric sensors, optical sensors, or the like.

Now referring primarily to FIG. 13B which provides a non-limiting stepwise method of operating (whether electromechanically or computer implemented) the particular embodiment of the microfluidic interface module (2) of FIG. 13A engaged to the particular embodiment of the CE chip (5) of FIG. 6. With respect to the step of priming (62) the CE chip (5), valve 2 (64), valve 4 (66), valve 5 (67) and valve 7 (69) can be established in the open condition and valve 1 (63) can be established in the open condition for a short duration of time and then valve 3 (65) can be established in the open condition to generate a flow path between the carrier fluid inlet (32) and the sample inlet (31) and to the cross channel inlet (34) and the cross channel outlet (35) of the CE chip (5) to deliver carrier fluid (12) to the first waste port (56) and the second waste port (57) and the third waste port (58).

In the step of sample loading (70) valve 4 (66), valve 5 (67), and valve 6 (68) can be established in the open condition to allow delivery of sample fluid (11) between the sample inlet (31) and the cross channel outlet (35) and cross channel inlet (34) of the CE chip (5) to the second waste port (57) and third waste port (58). The sample fluid (11) loaded in the sample leg (73) can be processed in the step of sample fluid analysis (89) generally above-described.

In the step of flushing (90), valve 2 (64), valve 4 (66), valve 5 (67), and valve 7 (69) can be established in the open condition to generate a flow path between the carrier fluid inlet (32) through the separation leg (74) and the first and second cross channel legs (72)(73) to the second and third waste ports (57)(58). The process can be repeated to serially process a plurality of different samples (11) without disengaging the CE chip (5) from the microfluidic interface module (2) which allows automated serial processing of a plurality of sample fluids (11).

The non-limiting embodiments of the microfluidic interface module (2) and CE chip (5) shown in FIGS. 12A and 13A, provide a general constructional form of the microfluidic interface (2) and CE chip (5) which can allow for placement of the carrier fluid inlet (32), the sample outlet (31), and the cross channel inlet (34) and the cross channel outlet (35) on the CE chip (5) in a numerous and wide variety of different locations to address a corresponding variety of capillary electrophoresis applications. The constructional form of the network of microfluidic interface channels (21) and pairs of bores (60) can also remain substantially as above described while the particular flow path configuration and placement of the bores (60) and attending valves (61) can readily be altered to accommodate the placement of inlets and outlets of a particular embodiment of the CE chip (5).

Now referring primarily to FIGS. 14-17, which provide enlarged views of the non-limiting embodiment of the microfluidic interface module (2) shown in FIGS. 4 and 13A fluidicly coupled to the non-limiting embodiment of the CE chip (5) of FIG. 6 by use of the microfluidic chip enclosure (6) of FIGS. 1-3 in the closed condition (92). FIG. 15 shows the cross section 15-15 shown in FIG. 14. The Figures along with the foregoing description providing an illustrative example by which a numerous and wide variety of embodiments of the microfluidic interface module (2) and CE chip (5) can be made and use by a person of ordinary skill.

Now referring primarily to FIGS. 18-20 which provide a general overview of the relationship of elements of an alternate embodiment of the inventive capillary electrophoresis system as shown in FIGS. 18-29. The embodiment shown in FIGS. 18-29 includes many the elements above described held in similar fixed relationship to accomplish the separation of substances (29) within embodiments of the CE chip (5). For brevity, those portions of the above description which apply to the corresponding elements of the embodiments shown in FIGS. 18-29 having the same numerical identifiers are not restated but are incorporated by reference. Differences in elements which share the same numerical indicator are described below. Understandably, a description of how to make and use additional new elements is set forth below.

Accordingly, referring primarily to FIGS. 18-21, alternate embodiments of the capillary electrophoresis system can include a support housing (1) configured to receive and operably position: a fluid transfer assembly (3), a microfluidic interface module (2), a manifold (as to certain embodiments) (100), a CE chip (5), a microfluidic chip enclosure (6), and an electrical interface (4) for conducting power from a power source (14) and electrical signals (18) to a computer processor (94).

Now referring primarily to FIG. 18, the fluid transfer assembly (3) further includes an internal standard transfer device (101) (such as a peristaltic pump, syringe pumps, reciprocating pumps, or like) which operates to transfer of an amount of internal standard (102) from an internal standard source (103) to a sample mixer (104). The sample transfer device (10) correspondingly operates to transfer an amount of sample fluid (11) from a sample fluid source (14) to the sample mixer (104). The amount of sample fluid (11) and the amount of internal standard (102) combined in the sample mixer (104) can be transferred to the sample supply port (9) of the microfluidic interface module (2). Similarly, the carrier fluid transfer device (16) (such as a peristaltic pump, syringe pumps, reciprocating pumps, or like) transfers an amount of an fluid (12) (such as carrier fluids, electrically conductive fluids, analysis fluid, or the like) from a fluid source (13) to the carrier fluid supply port (15) of the microfluidic interface module (2).

Now referring primarily to FIG. 21, which shows that particular embodiments of the microfluidic chip enclosure (6) operate between an closed condition (92) (as shown in FIG. 20) and an open condition (20) by release of the mechanical fastener (22) (in the form of a latch) which allows removable engagement of the CE chip (5) with the microfluidic interface module (2). The closed condition (92) sufficiently forcibly urges mated surfaces of the CE chip (5) and the microfluidic interface module (2) against each other to sealably fluidicly couple the network of microfluidic interface channels (21)(as shown for example in FIG. 26) in the microfluidic interface module (2) with the corresponding carrier channel (30) and cross channel (33) in the CE chip (5) (as shown for example in FIG. 27), as further described below. As shown by FIGS. 18-21, and by way of differentiation with the embodiment of FIGS. 1-4, the microfluidic chip enclosure (6) can be diposed in rotatable relation to the support housing (1) below the microfluid interface module (2). The microfluidic interface module (2) can be disposed in fixed relation to the support housing (1). Rotation of the microfluidic chip enclosure (6) in relation to the microfluidic interface module (2) from the closed condition (92) to the open condition (20) allows the CE chip (5) to be receivably retrieved in relation to the microfluidic chip enclosure (6). As to certain embodiments, the microfluidic chip enclosure (6) can provide a recess into which the CE chip (5) can be receivably retrieved. The microfluidic chip enclosure (6) can be maintained in the closed condition (92) by the operation of one or more mechanical fasteners (22) (shown as a latch in FIGS. 18-21) which draw the corresponding surfaces of the CE chip (5) and the microfluidic interface module (2) together for similar operation to that described for the embodiments of FIGS. 1-17.

As shown primarily in FIGS. 21-24, certain embodiments, can further include a manifold (100) having a first manifold face (106) and a second manifold face (107) disposed between the CE chip (5) and the microfluidic interface module (2). By rotation of the microfluidic chip enclosure (6), the inlets and outlets (31)(32)(34)(35) disposed on the second chip face (37) of the CE chip (5) can be sealably fluidicly coupled with the corresponding manifold ports (sample manifold port (121), cross channel inlet manifold port (122), cross channel outlet manifold port (123), carrier fluid inlet manifold port (124)) which communicate between the first the manifold face (106) and the second manifold face (107). The second manifold face (107) can engage the first module surface (48) of microfluidic interface module (2) to sealably fluidicly couple each manifold port (121)(122)(123)(124) with a corresponding microfluidic interface port (sample port (49), carrier fluid port (50), cross channel outlet port (51), and cross channel inlet port (52)).

Now referring primarily to FIGS. 22, 23 and 24, each manifold port (121)(122)(123)(124) can further provide a manifold port recess (126) which can take the form of a closed end cylindrical well open to the second manifold face (107) with the longitudinal axis co-axial with the corresponding manifold port (121)(122)(123)(124) disposed at the bottom of each manifold port recess (126). Each manifold port recess (126) can be dimensionally configured to insertingly receive a corresponding microfluidic interface port extension element (127). Each microfluidic interface port extension element (127) can be dimensionally configured to insert within a corresponding manifold port recess (126) to fluidicly couple the flow paths of each manifold port (121)(122)(123)(124) with the corresponding microfluidic interface ports (49)(50)(51)(52). As to the non-limiting example of FIGS. 22 and 25, the bottom surface (128) of each manifold port recess (126) sealably engages the terminal surface (129) of each extension element (127).

Using embodiments with the manifold (100) allows the manifold (100) to remain in fixed relation with the CE chip (5) by operation of mechanical fasteners (22), while the microfluidic interface module (2) can be engaged with the manifold (100) to deliver sample fluid (11) (including the internal standard (102) and carrier fluid (12) to the CE chip (5) and then be movably disengaged from the manifold (100). This allows separation of substances (29) within the CE chip (5) in two modes. First, as above-described, with the microfluidic interface module (5) sealably fluidicly coupled to manifold (100) to allow separation of substances (29) within the CE chip (5) in a sealed condition. Second, with the microfluidic interface module (2) movably disengaged from the manifold (100) to allow separation of substances (29) within the CE chip (5), as above-described, in an unsealed condition.

Now referring primarily to FIGS. 19-21 and 25-26, the microfluidic interface module (2) can be coupled to a movement assembly (108) which operates to engage and disengage the first manifold face (48) of the microfluidic interface module (2) with the second manifold face (107) of the manifold (100) or directly with the second chip face (37) of the CE chip (5). The non-limiting embodiment of a movement assembly (108) as shown in the Figures can include a plurality of guide shafts (109) each having an shaft end (110) coupled to the second manifold face (107) to dispose each of the plurality of guide shafts (109) in generally perpendicular relation to the second manifold face (107). The plurality of guide shafts (109) can each be located to slidely insert into a corresponding plurality of guide bores (111) (which may further include bushings as shown for example in FIG. 21) which communicate between the opposed module faces (45)(48) of the microfluidic interface module (2) allowing travel of the microfluidic interface module (2) in relation to the manifold (100). As to particular non-limiting embodiments, a spirally threaded bore (112) disposed generally on center in the microfluidic interface module (2) can rotating engage a first end (114) of a spirally threaded rod (113). The second end (115) of the spirally threaded rod (113) can be coupled to the shaft of a motor (116). Operation of the motor (116) having a fixed location above the microfluidic interface module (2), rotates the second end (115) of the spirally threaded rod (113) in the spirally threaded bore (112) to generate travel in the microfluidic interface module (2) toward the motor (116) (away from the manifold (100)). Rotating the second end (115) of the spirally threaded rod (113) in the opposite direction generates travel in the microfluidic interface module (2) away from the motor (116) (toward the manifold (100)) to correspondingly sealably fluidicly couple and uncouple the channels (21) of the microfluidic interface module (2) with the flow paths of the manifold (100) or the CE channels (27) of the CE chip (5). This non-limiting example is not intended to be limiting with respect the numerous and wide variety of movement assemblies (108) that can be used to generate travel in the microfluidic interface module (2) in relation to the manifold (100) or the CE chip (5). As but one additional example, the motor, treaded shaft and corresponding spirally threaded bore can be replace with a plunger solenoid (141) having a movable plunger (142) coupled to the microfluidic interface module (2).

Now referring primarily to FIG. 21, one or more high voltage pins (77) (also referred to as first circuit pins) and one or more detection pins (80) (also referred to as second circuit pins) can communicate between opposed first and second sides (104)(105) of the microfluidic chip enclosure (6) to provide a corresponding one or more first high voltage pin ends (78) which extend sufficiently outward from the first side (104) of the microfluidic chip enclosure (6) to engage electrical terminals (42) of the corresponding first circuit (38) and second circuit (39) disposed on the first face (37) of the CE chip (5) upon mated engagement of the CE chip (5) within the microfluidic chip enclosure (6). The one or more high voltage pins (77) can further provide one or more high voltage second pin ends (79) which extend outwardly from the first side (105) of the microfluidic chip enclosure (6) to electrically couple an external power source (17), as above-described. Similarly, the one or more detection pins (80) can provide a corresponding one or more second detection pin ends (93) which extend outwardly from the first side (105) of the microfluidic chip enclosure (6) to electrically couple an external analysis electronics module (19) of a computer processor (94), as above described, to any of a variety of detection elements (40), such as: amperometric sensors, conductivity sensors, voltametric sensors, optical sensors, or the like.

Now referring primarily FIGS. 25 and 26, an embodiment of the microfluidic interface module (2) can be produced to provide a network of microfluidic interface channels (21) which can be sealably fluidicly coupled to the corresponding CE channels (27) of the embodiment of the CE chip (5) shown in FIGS. 27-29 either directly or by use of the manifold (100) show in FIGS. 22-24 for the ingress and egress of carrier fluid (12) and sample fluid (11) (whether or not including internal standard (102)). While the microfluidic interface module (2) shown in FIGS. 25 and 26 is shown as a single integral piece, the embodiment can be produced generally as above described from two or more layers of substrate material (28) which are subsequently bonded together which as to the embodiment shown in FIGS. 25-26 has a generally rectangular volume which disposes a first module face (48) and a second module face (45) in substantially parallel opposed relation a distance apart bounded by four sides (55). Proximate each corner of the microfluidic interface module (2) one of the plurality of guide bores (111) communicates between the first module face (48) and the second module face (45). A sample fluid supply port (9) and a carrier fluid supply port (15) can be disposed on the first module face (48) which confers the advantage of shortening or reducing the volume of the microfluidic interface channels (21) between the fluid supply ports (9)(15) and the corresponding sample fluid port (49) and carrier fluid port (50). A first waste port (56), a second waste port (57) and a third waste port (58) can be disposed on one or more sides (55) of the microfluidic interface module (2).

Again referring primarily to FIGS. 25 and 26, one or more pair of bores (60) can be disposed at the second surface (45) of the microfluidic interface module (2) in dimensional relation which allows each of the pairs of bores (60) to be fluidicly coupled through a microfluidic valve (61) (also referred to as a "valve") coupled to the second module face (45) of the micofludic interface module (2). A non-limiting example of a microfluidic valve (61) suitable for use with embodiments of the microfluidic interface module (2) can be obtained from The Lee Company, Part No. LHDA 0521111.

Now referring primarily to FIG. 26, each one of the microfluidic valves (61) can operate between a closed condition which interrupts fluid flow between a pair of bores (60) and an open condition which allows fluid flow between a pair of bores (60). The valves (61) can each be activated or driven between the closed condition and the open condition based on an event schedule (75) (for example, the event schedule shown in FIG. 26A) to correspondingly alter the configuration of the flow paths within the network of microfluidic interface channels (21) to carry out each of a plurality steps (as non-limiting examples, the steps (62)(70) (89)(90) shown in FIG. 26A) of a method for use of embodiments of the microfluidic interface module (2) to process an amount of sample fluid (11) within a fluidicly coupled CE chip (5) (whether in the sealed condition or the unsealed condition). The event schedule (75) can be implemented by a computer processor (94) which operates in accordance with executable instructions of an event schedule computer program (76) to match the open condition and the closed condition of each valve (61) against a time schedule to provide one or more configurations of the flow paths within the network of microfluidic interface channels (21) of the microfluidic interface module (2) to carry out each of the plurality of steps in the event schedule (75).

Now referring primarily to FIGS. 26, 26A, and 27-29 which provides a non-limiting embodiment of an event schedule (75) including the steps of a method for use of the particular embodiment of the microfluidic interface module (2) shown in FIG. 26 fluidicly coupled to the particular embodiment of the CE chip (5) of FIGS. 27-29 to process an amount of sample fluid (11). The step of priming (62) the CE chip (5) prior to introduction of an amount of sample fluid (11) includes establishing valve 2 (64) and valve 5 (67) in the open condition which allows ingress of carrier fluid (12) from the carrier fluid supply port (15) through valve 2 (64) to deliver carrier fluid (12) to the cross channel inlet (34) and cross channel outlet (35) of the CE chip (5) and correspondingly to the second waste port (57). Priming the detection region (130) (see FIG. 30) of the carrier channel (30) by flowing carrier fluid (12) toward sample inlet (31), the carrier fluid (12) moves from a greater cross sectional area of the carrier fluid inlet (32) and carrier fluid inlet reservoir (117) and detection region (130) to the lesser cross sectional area of the separation leg (74) which confers an advantage of eliminating or reducing outgassing in the detection region (130) during the subsequent step of sample analysis (89) for detection of substances (29). Outgassing or the formation of bubbles in the detection region (130) of the carrier channel (30) can interfere with detection of separated substances (29) interrogated by the detection element (40). Opening valve 1 (63) for a short duration allows carrier fluid (12) to flow to the first waste port (56) to flush the carrier fluid inlet reservoir (117) as further described below. This step establishes the CE chip (5) in condition to receive an amount of sample fluid (11).

The event schedule (75) further includes the step of sample loading (70). The step of sample loading (70) includes establishing valve 3 (65) in the open condition to deliver an amount of sample fluid (11) from the sample supply port (9) of the microfluidic interface module (2) to the sample inlet (31) of the CE chip (5). Valve 4 can be established in the open condition for a short duration to flush the sample fluid inlet reservoir (118) as further described below. The CE chip (5) now primed with carrier fluid (11) and loaded with sample fluid (12) can now be operated as above described to separate and detect the substances (29) in the sample fluid (12).

With respect to electrophoretic processing of particular sample fluids (12) containing anions such as chloride (95), nitrate (96), and perchlorate (97) as above-described, the microfluidic interface module (2) can remain in sealed engagement with the CE chip (5) or the manifold (100), depending upon the embodiment, and separate these substances (29) from one another as shown in FIG. 32. However, as to other particular sample fluids (12) the electroosmotic flow within the carrier channel (30) can be sufficient during the period in which voltage is applied to create an imbalance in the hydrostatic pressure between the respective fluid reservoirs (117)(118)(119)(120) of the CE chip (5) when sealed to the microfluidic interface module (2). This imbalance can interfere with separation of substances (29) in the separation leg (74) of the carrier channel (30). Accordingly, before the sample analysis step (89), the microfluidic interface module (2) can be fluidically disengaged from the CE chip (5) or the manifold (100) depending upon the embodiment.

In the step of sample analysis (89), each of the valves (63)(64)(65)(66)(67) can be established in the closed condition and sample fluid (12) processing proceeds substantially as above-described for other embodiments.

Again referring to FIGS. 26, 26A and 27-29, the method can further include the step of flushing (90) the CE chip (5) after the step of sample fluid analysis (89). As shown in FIG. 26A the flushing (90) step can be achieved by opening valve 2 (64), valve 4 (66), and valve 5 (67) to allow carrier fluid (12) to be delivered through the carrier channel (30) and through the first and second cross channel legs (71) (72) to the cross channel inlet (34) and the cross channel outlet (35) and to the second waste port (57). The carrier fluid (12) is further delivered to the sample inlet (31) which allows egress of the carrier fluid (12) from the third waste port (56), as further described below. The steps in the method can be repeated to automatically run a plurality of fluid samples (11) in serial order from one or a plurality of different sample sources (14) whether in the sealed condition or in the unsealed condition.

Now referring primarily to FIGS. 27-29 and 30-31, embodiments of the CE chip (5) can provide the carrier channel (30) disposed between a carrier fluid reservoir (117) and sample fluid reservoir (118) the reservoirs functioning as the carrier fluid inlet (32) and the sample fluid inlet (31). Similarly, the cross channel (33) can be disposed between a first cross channel reservoir (119) and a second cross channel reservoir (120) which further serve as the cross channel inlet (34) and the cross channel outlet (35). As above-described, each reservoir (117)(118)(119)(120) must have sufficient volume to facilitate electro-osmotic flow within the carrier channel (30) and within the cross channel (33) during the period in which voltage is applied between the reservoirs (117)(118)(119)(120) (see FIGS. 27-29). Now referring primarily to FIG. 31, each of the reservoirs (117) (118)(119)(120) can generally take the form of a closed end cylinder with the opening communicating with the second chip face (37) of the CE chip (5); however, the invention is not so limited and the reservoirs (117)(118)(119)(120) can have any configuration which can be disposed in the CE chip (5), fluidically coupled to the corresponding channel (30)(33), and which can be sealably fluidically coupled to the flow paths of the manifold (100) or the microfluidic interface module (2). As shown in FIG. 31, a high voltage pin (77) can communicate with the internal volume of each reservoir (117)(118)(119)(120).

Now referring primarily to FIG. 30, embodiments of the CE chip (5) can further provide a carrier channel (33) having a separation leg (74) and a detection region (130), the detection region (130) having a greater width than the separation let (74). As to certain embodiments of the CE chip (5), the separation region (74) can have a width of about 50 μm and the width of the detection region can be about 200 μm; however, the invention is not so limited and the width of the separation leg (74) and the detection region (130) can vary depending upon the application. The detection region (130) can be fluidicly coupled to the carrier fluid reservoir (117) above described. A detection element (84) can be disposed in generally transverse relation to the detection region (130) and operate as above described.

Now referring primarily to FIG. 31, each of the reservoirs (117)(118)(119)(120) can be sealably fluidicly coupled to a corresponding microfluidic interface port (49)(50)(51)(52) of the microfluidic interface module (2) as illustrated by the embodiments shown by FIGS. 1-17 or by the corresponding manifold port (121)(122)(123)(124) as illustrated by the embodiments shown by FIGS. 18-31. As to particular embodiments, whether or not including the manifold (100), one or more of the microfluidic interface ports (49)(50)(51) (52) correspondingly coupled to one or more reservoirs (117)(118)(119)(120) can be configured to rinse or flush the reservoir. As to these embodiments, the microfluidic interface ports (49)(50)(51)(52) can be configured as a co-axial flow path (131) with the first flow path (132) surrounded by the second flow path (133) in co-axial relation. The first flow path (132) can be configured as a conduit (134) (typically having a cylindrical external surface defining a cylindrical flow path within) which extends centrally through the co-axial flow path (131) and can extend a distance outwardly from the second face (45) of the microfluidic interface module (2). Upon sealed fluidic coupling of the microfluidic interface module (2), the conduit end (135) of the conduit (135) can be disposed within the corresponding reservoir (117)(118)(119)(120) of the CE chip (5). Fluid (11)(12) can be expelled from the conduit end (135) of the conduit (135) within the reservoir (117)(118)(119)(120) with sufficient force and for a sufficient period of time to flush the internal volume and sidewalls of the reservoir (117)(118)(119)(120). The second flow path (133) co-axially surrounding the first flow path (132) can provide sufficient volume for egress of the fluid (11)(12) expelled from the end (135) of the cylindrical conduit (134). The second flow path (133) terminates a distance inward of the first module face (48) of the microfluidic interface module (2) in a non-co-axial flow path (136) correspondingly fluidically coupled to a waste port (56)(57)(58).

Now referring primarily to FIG. 32, detector response (88) plotted over time (87) evidences the separation of substances (29) (for example, anions, such as chloride (95), nitrate (96), perchlorate (97) along with an internal standard (98) within an amount of sample fluid (11). The separation of anions can be achieved using the embodiments of the microfluidic interface module (2) of FIGS. 4 and 13A or 21 and 26 sealably fluidicly coupled to a corresponding embodiment of the CE chip (5) of FIGS. 6 and 27 using the corresponding stepwise methods of FIGS. 13B and 26A. Each of the substances (29) within the amount of sample fluid (11) were separated within the separation leg (74) of the CE chip (5) with detection based on electrical conductivity between the pair of electrodes (92) intersecting the microfluidic channel of the separation leg (74) at the detection location (85) proximate the carrier fluid inlet (32). The pair of electrodes can be disposed within the separation leg (74) to directly contact with the carrier fluid (11) within the separation leg (74). Accordingly, as separated substances (29) pass through the detection location (85) of the separation leg (74) between the pair of electrodes (92) conductivity increases and as substances (29) travel beyond the pair of electrodes (92) conductivity decreases to the background (141) associated with the carrier fluid (12). A standard or a mixture of standards for each substance (29) to be separated by capillary electrophoresis and detected by conductivity or other detection means can be run under controlled conditions in the desired configuration of a CE channel (27) to produce CE channel standard data (87) against which substances (29) in sample fluids (11) can be compared in terms of electrophoretic mobility (87) and detection signal amplitude (88) such that substances (29) in each amount of sample fluid (11) analyzed in the CE chip (5) can be identified and the concentration of the substance in a sample fluid determined by the functionalities of the external analysis electronics (19).

Now referring primarily to FIG. 33, detector response (88) plotted over time (87) evidences the separation of substances (29) (for example, cation, such as potassium (137), calcium (138), magnesium (39) and sodium (140)) within an amount of sample fluid (11). The separation of cations such as potassium (can be achieved using the embodiments of the microfluidic interface module (2) of 21 and 26 (or other embodiments) which can be sealably fluidicly coupled to a corresponding embodiment of the CE chip (5) of 27 for the priming (62), sample loading (70) and flushing (90) steps of the method shown in FIG. 26A but can be uncoupled from the CE chip (5) for the sample analysis step (89) in which substances (29) are separated and detected within the separation leg (74) of the CE chip (5). Each of the substances within the amount of sample fluid (11) were separated within the separation leg (74) of the CE chip (5) with detection and based on electrical conductivity between the pair of electrodes (92), as above-described.

As can be easily understood from the foregoing, the basic concepts of the present invention may be embodied in a variety of ways. The invention involves numerous and varied embodiments, including the best mode, of a capillary electrophoresis system which provides a microfluidic chip for capillary electrophoresis and a microfluidic interface module which fluidicly couples the microfluidic chip to external fluid sources and or external repositories.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "interface" should be understood to encompass disclosure of the act of "interfacing"—whether explicitly discussed or not—and, conversely, were there effectively disclosure of the act of "interfacing", such a disclosure should be understood to encompass disclosure of "an interface" and even a "means for interfacing." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the capillary electrophoresis systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A microfluidic capillary electrophoresis apparatus, comprising:
a CE chip having a first chip face and a second chip face disposed in substantially opposed planar relation a sufficient distance apart to have disposed within a carrier channel intersected by a cross channel, said carrier channel and said cross channel each communicating with said first face of said CE chip in an inlet and an outlet;
a microfluidic interface module having a first module face and a second module face disposed in substantially opposed planar relation a sufficient distance apart to have disposed within a plurality of microfluidic interface channels each communicating with said first module face in a plurality of interface ports each having a location on said first module face to correspondingly sealably fluidically couple one of said inlet or said outlet of said CE chip to direct a sample fluid or a carrier fluid in a flow path between a supply port and a waste port of said microfluidic interface module;
a movement assembly adapted to generate sufficient travel in said microfluidic interface module in a first direction to correspondingly sealably fluidically couple each of said plurality of interface ports to each said inlet and said outlet of said CE chip and in a second direction to fluidicly uncouple each of said plurality of ports from each said inlet and said outlet of said CE chip; and
a switchable solenoid valve disposed in relation to at least one of said plurality of microfluidic interface channels, said switchable solenoid valve operable in response to electrical signals to provide an open condition and a closed condition of said at least one of said plurality of microfluidic interface channels to regulate flow of said sample fluid or said carrier fluid between said supply port and said waste port.

2. The microfluidic capillary electrophoresis apparatus of claim 1, wherein each said plurality of interface ports of said microfluidic interface module communicates with said first module face in a co-axial flow path having a first flow path co-axially surrounded by a second flow path, wherein each said inlet and each said outlet of said CE chip communicates with said first chip face in a fluid reservoir, and wherein said first flow path will direct said carrier fluid or sample fluid to said fluid reservoir and said second flow path will direct said carrier fluid or said sample fluid away from said reservoir.

3. The microfluidic capillary electrophoresis apparatus of claim 2, wherein said co-axial flow path comprises an interface port recess through which a conduit co-axially passes to extend a distance sufficiently outward of said first module face of said microfluidic interface module to correspondingly locate a conduit end within said reservoir, said conduit defining said first flow path of said co-axial flow path and said interface port recess co-axially surrounding said conduit defining said second flow path of said co-axial flow path.

4. The microfluidic capillary electrophoresis apparatus of claim 3, wherein said first flow path of said co-axial flow path switchably fluidicly couples to said supply port and said second flow path of said co-axial flow path switchably fluidicly couples to said waste port, wherein said first flow path in said open condition and said second flow path in said closed condition will direct said sample fluid or said carrier fluid to said carrier channel or to said cross channel, and wherein said first flow path of said co-axial flow path in said open condition and said second flow path of said co-axial flow path in said open condition will direct said carrier fluid or said sample fluid to said waste port.

5. The microfluidic capillary electrophoresis apparatus of claim 1, further comprising a manifold having a first manifold face and a second manifold face disposed in substantially opposed planar relation a distance apart and having a plurality of manifold ports which communicate between said first manifold face and said second manifold face, each of said plurality of manifold ports of said first manifold face having a location to correspondingly sealably fluidicly couple a corresponding one of said plurality of interface ports of said microfluidic interface module and each of said plurality of manifold ports of said second manifold face having a location to correspondingly sealably fluidicly couple a corresponding one of said inlet or said outlet of said CE chip.

6. The microfluidic capillary electrophoresis apparatus of claim 5, further comprising a CE chip enclosure which receives in fixed relation said CE chip, said CE chip enclosure being movable to releasably sealably fluidicly couple each said inlet and said outlet of said CE chip with said plurality of interface ports of said microfluidic interface module or said plurality of manifold ports of said manifold.

7. The microfluidic capillary electrophoresis apparatus of claim 6, wherein said CE chip enclosure is rotatable in relation to said microfluidic interface module or said manifold to correspondingly sealably fluidicly couple each of said inlet and said outlet of said CE chip with said plurality of interface ports of said microfluidic interface module or said plurality of manifold ports of said manifold.

8. The microfluidic capillary electrophoresis apparatus of claim 7, wherein said CE chip enclosure is rotatable to sealably fluidicly couple each said inlet and said outlet of said CE chip with said plurality of manifold ports of said manifold, and wherein said movement assembly is adapted to generate sufficient travel in said microfluidic interface module in a first direction to correspondingly sealably fluidicly couple said plurality of interface ports of said microfluidic interface module with said plurality of manifold ports of said manifold and is adapted to generate sufficient travel in a second direction to fluidicly uncouple said plurality of interface ports of said microfluidic interface module from said plurality of manifold ports of said manifold.

9. The microfluidic capillary electrophoresis apparatus of claim 8, further comprising a plurality of high voltage pins which communicate between a first enclosure face and a second enclosure face of said microfluidic chip enclosure, each of said plurality of high voltage pins extending a distance outward of said first enclosure face to correspondingly contact an electrical terminal of a first electrical circuit which applies a high voltage between opposed ends of said carrier channel and opposed ends of said cross channel, and each of said high voltage pins extending a distance outward of said second enclosure face to electrically couple to an external power source.

10. The microfluidic capillary electrophoresis apparatus of claim 9, further comprising one or more detection pins which communicate between a first enclosure face and a second enclosure face of said microfluidic chip enclosure, each of said one or more detection pins extending a distance outward of said first enclosure face to correspondingly contact an electrical terminal of a second electrical circuit including a detector located to interrogate at least one substance within said carrier channel of said CE chip, and each of said one or more detection pins extending a distance outward of said second enclosure face to electrically couple to an external analysis electronics which receives an electrical signal from said detector.

11. The microfluidic capillary electrophoresis apparatus of claim 1, wherein said at least one of said plurality of microfluidic interface channels between said supply port and said waste port communicates with said second module face of said microfluidic interface module in a pair of bores, and wherein said switchable valve fluidicly couples said pair of bores to generate said open condition of said at least one of said plurality of microfluidic interface channels.

12. The microfluidic capillary electrophoresis apparatus of claim 11, further comprising a computer processor which operates to match the open condition and the closed condition of each switchable valve against a time schedule to provide one or more configurations of said at least one of said plurality of microfluidic interface channels of said microfluidic interface module to perform each of a plurality of steps in an event schedule.

13. A microfluidic capillary electrophoresis apparatus, comprising:
    a CE chip having a first chip face and a second chip face disposed in substantially opposed planar relation a sufficient distance apart to have disposed within a carrier channel intersected by a cross channel, said carrier channel and said cross channel each communicating with said first face of said CE chip in an inlet and an outlet;
    a microfluidic interface module having a first module face and a second module face disposed in substantially opposed planar relation a sufficient distance apart to have disposed within a plurality of microfluidic interface channels each communicating with said first module face in a plurality of interface ports each having a location on said first module face to correspondingly sealably fluidicly couple one of said inlet or said outlet of said CE chip to direct a sample fluid or a carrier fluid in a flow path between a supply port and a waste port of said microfluidic interface module;
    a plurality of high voltage pins which communicate between the first module face and the second module face of said microfluidic interface module, each of said plurality of high voltage pins extending a distance outward of said first face of said microfluidic interface module to correspondingly contact an electrical terminal of a first electrical circuit which applies a high voltage between opposed ends of said carrier channel and opposed ends of said cross channel, and each of said high voltage pins extending a distance outward of said second face to electrically couple to an external power source; and
    a switchable solenoid valve disposed in relation to at least one of said plurality of microfluidic interface channels, said switchable solenoid valve operable in response to electrical signals to provide an open condition and a closed condition of said at least one of said plurality of microfluidic interface channels to regulate flow of said sample fluid or said carrier fluid between said supply port and said waste port.

14. The microfluidic capillary electrophoresis apparatus of claim 13, further comprising one or more detection pins which communicate between the first module face and the second module face of said microfluidic interface module, each of said one more detection pins extending a distance outward of said first module face to correspondingly contact an electrical terminal of a second electrical circuit which includes a detector located to interrogate at least one substance within said carrier channel of said CE chip, and each of said one or more detection pins extending a distance outward of said second manifold face to electrically couple to an external analysis electronics which receives an electrical signal from said detector.

15. The microfluidic capillary electrophoresis apparatus of any one of claim 10 or 14, wherein said external analysis electronics is adapted to transform said signal received from said detector into a detection signal amplitude which varies based upon a detected amount of said substance within said carrier channel.

16. A microfluidic capillary electrophoresis apparatus, comprising:
- a CE chip having a first chip face and a second chip face disposed in substantially opposed planar relation a sufficient distance apart to have disposed within a carrier channel intersected by a cross channel, said carrier channel and said cross channel each communicating with said first face of said CE chip in an inlet and an outlet;
- a microfluidic interface module having a first module face and a second module face disposed in substantially opposed planar relation a sufficient distance apart to have disposed within a plurality of microfluidic interface channels each communicating with said first module face in a plurality of interface ports each having a location on said first module face to correspondingly sealably fluidicly couple one of said inlet or said outlet of said CE chip to direct a sample fluid or a carrier fluid in a flow path between a supply port and a waste port of said microfluidic interface module; and
- a switchable valve disposed in relation to at least one of said plurality of microfluidic interface channels, said switchable valve operable to provide an open condition and a closed condition of said at least one of said plurality of microfluidic interface channels to regulate flow of said sample fluid or said carrier fluid between said supply port and said waste port;
- wherein each said plurality of interface ports of said microfluidic interface module communicates with said first module face in a co-axial flow path having a first flow path co-axially surrounded by a second flow path;
- wherein each said inlet and each said outlet of said CE chip communicates with said first chip face in a fluid reservoir; and
- wherein said first flow path will direct said carrier fluid or sample fluid to said fluid reservoir and said second flow path will direct said carrier fluid or said sample fluid away from said reservoir.

17. A microfluidic capillary electrophoresis apparatus, comprising:
- a CE chip having a first chip face and a second chip face disposed in substantially opposed planar relation a sufficient distance apart to have disposed within a carrier channel intersected by a cross channel, said carrier channel and said cross channel each communicating with said first face of said CE chip in an inlet and an outlet;
- a microfluidic interface module having a first module face and a second module face disposed in substantially opposed planar relation a sufficient distance apart to have disposed within a plurality of microfluidic interface channels each communicating with said first module face in a plurality of interface ports each having a location on said first module face to correspondingly sealably fluidicly couple one of said inlet or said outlet of said CE chip to direct a sample fluid or a carrier fluid in a flow path between a supply port and a waste port of said microfluidic interface module;
- a manifold having a first manifold face and a second manifold face disposed in substantially opposed planar relation a distance apart and having a plurality of manifold ports which communicate between said first manifold face and said second manifold face, each of said plurality of manifold ports of said first manifold face having a location to correspondingly sealably fluidicly couple a corresponding one of said plurality of interface ports of said microfluidic interface module, and each of said plurality of manifold ports of said second manifold face having a location to correspondingly sealably fluidicly couple a corresponding one of said inlet or said outlet of said CE chip; and
- a switchable valve disposed in relation to at least one of said plurality of microfluidic interface channels, said switchable valve operable to provide an open condition and a closed condition of said at least one of said plurality of microfluidic interface channels to regulate flow of said sample fluid or said carrier fluid between said supply port and said waste port.

* * * * *